(12) United States Patent
Johnson et al.

(10) Patent No.: US 10,711,067 B2
(45) Date of Patent: Jul. 14, 2020

(54) TREATMENT OF POST-PRANDIAL HYPERINSULINEMIA AND HYPOGLYCEMIA AFTER BARIATRIC SURGERY

(71) Applicant: XOMA (US) LLC, Berkeley, CA (US)

(72) Inventors: Kirk W. Johnson, Moraga, CA (US); Rajneesh Nath, Los Altos Hills, CA (US); Paul Rubin, San Francisco, CA (US)

(73) Assignee: XOMA (US) LLC, Emeryville, CA (US)

(*) Notice: Subject to any disclaimer, the term of this patent is extended or adjusted under 35 U.S.C. 154(b) by 3 days.

(21) Appl. No.: 15/555,608

(22) PCT Filed: Mar. 3, 2016

(86) PCT No.: PCT/US2016/020539
§ 371 (c)(1),
(2) Date: Sep. 5, 2017

(87) PCT Pub. No.: WO2016/141111
PCT Pub. Date: Sep. 9, 2016

(65) Prior Publication Data
US 2018/0037658 A1    Feb. 8, 2018

Related U.S. Application Data

(60) Provisional application No. 62/288,955, filed on Jan. 29, 2016, provisional application No. 62/127,788, filed on Mar. 3, 2015.

(51) Int. Cl.
*C07K 16/28* (2006.01)
*A61K 9/00* (2006.01)
*A61K 39/395* (2006.01)
*A61K 39/00* (2006.01)

(52) U.S. Cl.
CPC ........ *C07K 16/2869* (2013.01); *A61K 9/0019* (2013.01); *A61K 39/3955* (2013.01); *A61K 2039/505* (2013.01); *A61K 2039/54* (2013.01); *A61K 2039/545* (2013.01); *C07K 2317/21* (2013.01); *C07K 2317/56* (2013.01); *C07K 2317/565* (2013.01); *C07K 2317/76* (2013.01); *C07K 2317/92* (2013.01)

(58) Field of Classification Search
CPC .................. C07K 16/2869; A61K 39/3955
See application file for complete search history.

(56) References Cited

U.S. PATENT DOCUMENTS

| | | |
|---|---|---|
| 4,179,337 A | 12/1979 | Davis et al. |
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 4,975,278 A | 12/1990 | Senter et al. |
| 5,057,313 A | 10/1991 | Shih et al. |
| 5,122,469 A | 6/1992 | Mather et al. |
| 5,223,409 A | 6/1993 | Ladner et al. |
| 5,229,275 A | 7/1993 | Goroff |
| 5,348,867 A | 9/1994 | Georgiou et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,589,369 A | 12/1996 | Seidman et al. |
| 5,591,669 A | 1/1997 | Krimpenfort et al. |
| 5,643,768 A | 7/1997 | Kawasaki |
| 5,658,754 A | 8/1997 | Kawasaki |
| 5,723,287 A | 3/1998 | Russell et al. |
| 5,766,886 A | 6/1998 | Studnicka et al. |
| 5,770,429 A | 6/1998 | Lonberg et al. |
| 5,877,293 A | 3/1999 | Adair et al. |
| 5,939,598 A | 8/1999 | Kucherlapati et al. |
| 5,969,108 A | 10/1999 | McCafferty et al. |
| 6,054,287 A | 4/2000 | Gao et al. |
| 6,091,001 A | 7/2000 | Jakobovits et al. |
| 6,114,598 A | 9/2000 | Kucherlapati et al. |
| 6,194,551 B1 | 2/2001 | Idusogie et al. |
| 6,306,393 B1 | 10/2001 | Goldenberg |
| 6,657,103 B1 | 12/2003 | Kucherlapati et al. |
| 6,660,843 B1 | 12/2003 | Feige et al. |
| 6,699,658 B1 | 3/2004 | Wittrup et al. |
| 6,833,268 B1 | 12/2004 | Green et al. |

(Continued)

FOREIGN PATENT DOCUMENTS

| EP | 0404097 A2 | 12/1990 |
|---|---|---|
| WO | WO-81/01145 A1 | 4/1981 |

(Continued)

OTHER PUBLICATIONS

Chamow and Ashkenazi, Tibtech 14: 52-60, 1996.*
Rudikoff et al., Proc. Natl. Acad. Sci. 79: 1979-1983, 1982.*
Abrahamsson et al., GLP1 analogs as treatment of postprandial hypoglycemia following gastric bypass surgery: a potential new indication, Eur. J. Endocrinol., 169(6):885-9 (2013).
Adams et al., Structure and function of the type 1 insulin-like growth factor receptor, Cell Mol. Life Sci., 57(7):1050-93 (2000).
Amstutz et al., In vitro display technologies: novel developments and applications, Curr. Opin. Biotechnol., 12(4):400-5 (2001).
Arnoux et al., Congenital hyperinsulinism: current trends in diagnosis and therapy, Orphanet J. Rare Dis., 6:63 (2011).
Barbas et al., Assembly of combinatorial antibody libraries on phage surfaces: the gene III site, Proc. Natl. Acad. Sci. USA, 88(18):7978-82 (1991).

(Continued)

*Primary Examiner* — Gyan Chandra
(74) *Attorney, Agent, or Firm* — Marshall, Gerstein & Borun LLP

(57) ABSTRACT

The present disclosure relates, in general, to methods of treating or preventing post-prandial hypoglycemia after gastric bypass surgery using a negative modulator antibody that binds to the insulin receptor and modulates the action of insulin at the insulin receptor.

24 Claims, 5 Drawing Sheets
Specification includes a Sequence Listing.

(56) References Cited

U.S. PATENT DOCUMENTS

| | | |
|---|---|---|
| 8,926,976 B2 | 1/2015 | Corbin et al. |
| 9,885,711 B2 | 2/2018 | White et al. |
| 9,944,698 B2 | 4/2018 | Corbin et al. |
| 2002/0004215 A1 | 1/2002 | Osbourn et al. |
| 2002/0199213 A1 | 12/2002 | Tomizuka et al. |
| 2003/0031667 A1 | 2/2003 | Deo et al. |
| 2003/0044772 A1 | 3/2003 | Watkins et al. |
| 2003/0092125 A1 | 5/2003 | Davis et al. |
| 2003/0118592 A1 | 6/2003 | Ledbetter et al. |
| 2003/0133939 A1 | 7/2003 | Ledbetter et al. |
| 2003/0190317 A1 | 10/2003 | Baca et al. |
| 2003/0194404 A1 | 10/2003 | Greenfeder et al. |
| 2005/0037421 A1 | 2/2005 | Honda et al. |
| 2005/0136049 A1 | 6/2005 | Ledbetter et al. |
| 2011/0076284 A1* | 3/2011 | Corbin .................. C07K 16/26 424/172.1 |

FOREIGN PATENT DOCUMENTS

| | | |
|---|---|---|
| WO | WO-87/00195 A1 | 1/1987 |
| WO | WO-88/07378 A1 | 10/1988 |
| WO | WO-91/00906 A1 | 1/1991 |
| WO | WO-91/017271 A1 | 11/1991 |
| WO | WO-91/17271 A1 | 11/1991 |
| WO | WO-92/01047 A1 | 1/1992 |
| WO | WO-92/001047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-93/11161 A1 | 6/1993 |
| WO | WO-94/02602 A1 | 2/1994 |
| WO | WO-96/11953 A1 | 4/1996 |
| WO | WO-96/30498 A1 | 10/1996 |
| WO | WO-96/32478 A1 | 10/1996 |
| WO | WO-96/33735 A1 | 10/1996 |
| WO | WO-96/34096 A1 | 10/1996 |
| WO | WO-97/34631 A1 | 9/1997 |
| WO | WO-98/024893 A2 | 6/1998 |
| WO | WO-03/041600 A1 | 5/2003 |
| WO | WO-2008/085982 A2 | 7/2008 |
| WO | WO-2010/003939 A1 | 1/2010 |
| WO | WO-2011/038302 A2 | 3/2011 |

OTHER PUBLICATIONS

Barnes et al., Methods for growth of cultured cells in serum-free medium, Anal. Biochem., 102(2):255-70 (1980).

Batra et al., Recombinant anti-erbB2 immunotoxins containing Pseudomonas exotoxin, Proc. Natl. Acad. Sci. USA, 89(13):5867-71 (1992).

Bayer et al., The avidin-biotin complex in affinity cytochemistry, Methods Enzymol., 62:308-15 (1979).

Becker et al., An antibody-interleukin 2 fusion protein overcomes tumor heterogeneity by induction of a cellular immune response, Proc. Natl. Acad. Sci. USA, 93(15):7826-31 (1996).

Better et al., Escherichia coli secretion of an active chimeric antibody fragment, Science, 240(4855):1041-3 (1988).

Biocca et al., Expression and targeting of intracellular antibodies in mammalian cellls. Embo. 9: 101-8 (1990).

Birch et al., Antibody production, Adv. Drug Deliv. Rev., 58(5-6):671-85 (2006).

Bird et al., Single-chain antigen binding protein. Science . 242: 423-6 (1988).

Boleti et al., Construction, expression and characterisation of a single chain anti-tumour antibody (scFv)-IL-2 (fusion protein, Ann. Oncol., 6(9):945-7 (1995).

Boulianne et al., Production of functional chimaeric mouse/human antibody. Nature. 312: 643-6 (1984).

Brinkmann et al., B3(Fv)-PE38KDEL, a single-chain immunotoxin that causes complete regression of a human carcinoma in mice, Proc. Natl. Acad. Sci. USA, 88(19):8616-20 (1991).

Bruggermann et al., Designer mice: the production of human antibody repertoires in transgenic animals, Year Immunol., 7:33-40 (1993).

Burton et al., Human antibodies from combinatorial libraries, Adv. Immunol., 57:191-280 (1994).

Caron et al., Engineered humanized dimeric forms of IgG are more effective antibodies, J. Exp. Med., 176(4):1191-5 (1992).

Carter et al., High level Escherichia coli expression and production of a bivalent humanized antibody fragment. Bio/Technology 10: 163-7 (1992).

Caton et al., Influenza virus hemagglutinin-specific antibodies isolated from a combinatorial expression library are closely related to the immune response of the donor, Proc. Natl. Acad. Sci. USA, 87(16):6450-4 (1990).

Chaudhary et al., A recombinant immunotoxin consisting of two antibody variable domains fused to Pseudomonas exotoxin, Nature, 339(6223):394-7 (1989).

Chothia et al., Canonical structures for the hypervariable regions of immunoglobulins, J. Mol. Biol., 196(4):901-17 (1987).

Chothia et al., Conformations of immunoglobulin hypervariable regions, Nature, 342(6252):877-83 (1989).

Clackson et al., In vitro selection from protein and peptide libraries, Trends Biotechnol., 12(5):173-84 (1994).

Clackson et al., Making antibody fragments using phage display libraries, Nature, 352(6336):624-8 (1991).

Colby et al., Potent inhibition of huntingtin aggregation and cytotoxicity by a disulfide bond-free single-domain intracellular antibody. Proc Natl Acad Sci USA. 101: 17616-21 (2004).

Conrath et al., Beta-lactamase inhibitors derived from single-domain antibody fragments elicited in the camelidae, Antimicrob. Agents Chemother., 45(10):2807-12 (2001).

Cortez-Retamozo et al., Efficient cancer therapy with a nanobody-based conjugate, Cancer Res., 64(8):2853-7 (2004).

De Meyts, Insulin and its receptor: structure, function and evolution, Bioessays, 26(12):1351-62 (2004).

Denley et al., Structural determinants for high-affinity binding of insulin-like growth factor II to insulin receptor (IR)-A, the exon 11 minus isoform of the IR, Mol. Endocrinol., 18(10:2502-12 (2004).

Denley et al., The insulin receptor isoform exon 11—(IR-A) in cancer and other diseases: a review, Horm. Metab. Res., 35(11-12):778-85 (2003).

Deonarain et al., Construction, refolding and cytotoxicity of a single chain Fv-seminal ribonuclease fusion protein expressed in Escherichia coli, Tumor Targeting, 1:177 (1995).

Desmyter et al., Antigen specificity and high affinity binding provided by one single loop of a camel single-domain antibody, J. Biol. Chem., 276(28):26285-90 (2001).

Dohlsten et al., Monoclonal antibody-superantigen fusion proteins: tumor-specific agents for T-cell-based tumor therapy, Proc. Natl. Acad. Sci. USA, 91(19):8945-9 (1994).

Doronina et al., Development of potent monoclonal antibody auristatin conjugates for cancer therapy, Nat. Biotechnol., 21(7):778-84 (2003).

Douillard et al., Hypoglycaemia related to inherited metabolic diseases in adults, Orphanet J. Rare Dis., 7:26 (2012).

Duckworth et al., Insulin degradation: progress and potential, Endocr. Rev., 19(5):608-24 (1998).

Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).

Evan et al., Isolation of monoclonal antibodies specific for human c-myc proto-oncogene product, Mol. Cell Biol., 5(12):3610-6 (1985).

Ewert et al., Biophysical properties of camelid $V_{HH}$ domains compared to those of human $V_H3$ domains. Biochemisrty 41: 3628-36 (2002).

Ferrara et al., Modulation of therapeutic antibody effector functions by glycosylation engineering: influence of Golgi enzyme localization domain and co-expression of heterologous betal, 4-N-acetylglucosaminyltransferase III and Golgi alpha-mannosidase II, Biotechnol. Bioeng., 93(5):851-61 (2006).

Field et al., Purification of a RAS-responsive adenylyl cyclase complex from Saccharomyces cerevisiae by use of an epitope addition method, Mol. Cell Biol., 8(5):2159-65 (1988).

(56) References Cited

OTHER PUBLICATIONS

Fishwild et al., High-avidity human IgG kappa monoclonal antibodies from a novel strain of minilocus transgenic mice, Nat. Biotechnol., 14(7):845-51 (1996).
Fix, Strategies for delivery of peptides utilizing absorption-enhancing agents, J. Pharm. Sci., 85(12):1282-5 (1996).
Fominaya et al., Target cell-specific DNA transfer mediated by a chimeric multidomain protein. Novel non-viral gene delivery system, J. Biol. Chem., 271(18):10560-8 (1996).
Friedman et al., Antitumor activity of the single-chain immunotoxin BR96 sFv-PE40 against established breast and lung tumor xenografts, J. Immunol., 150(7):3054-61 (1991).
Fuchs et al., Targeting recombinant antibodies to the surface of *Escherichia coli*: fusion to a peptidoglycan associated lipoprotein, Bio/Technology, 9:1369-73 (Dec. 1991).
Garrard et al., Fab assembly and enrichment in a monovalent phage display system, Bio/Technology, 9(12):1373-7 (1991).
Gebauer et al., Engineered protein scaffolds as next-generation antibody therapeutics, Curr. Opin. Chem. Biol., 13(3):245-55 (2009).
Gill et al., Biopharmaceutical drug discovery using novel protein scaffolds, Curr. Opin. Biotechnol., 17(6):653-8 (2006).
Goding, Conjugation of antibodies with fluorochromes: modifications to the standard methods, J. Immunol. Methods, 13(3-4):215-26 (1976).
Goldenberg, New developments in monoclonal antibodies for cancer detection and therapy, CA Cancer J. Clin., 44(1):43-64 (1994).
Graham et al., Characteristics of a human cell line transformed by DNA from human adenovirus type 5. J. Gen. Virol. 36: 59-74 (1977).
Gram et al., In vitro selection and affinity maturation of antibodies from a naive combinatorial immunoglobulin library, Proc. Natl. Acad. Sci. USA, 89(8):3576-80 (1992).
Greenberg et al., A new antigen receptor gene family that undergoes rearrangement and extensive somatic diversification in sharks, Nature, 374(6518):168-73 (1995).
Griffiths et al., Human anti-self antibodies with high specificity from phage display libraries, Embo J., 12(2):725-34 (1993).
Guss et al., Structure of the IgG-binding regions of streptococcal protein G. Embo 5: 1567-75 (1986).
Ham et al., Media and growth requirements, Methods Enzymol., 58:44-93 (1979).
Hamers-Casterman et al., Naturally occurring antibodies devoid of light chains, Nature, 363(6428):446-8 (1993).
Hanes et al., In vitro selection and evolution of functional proteins by using ribosome display, Proc. Natl. Acad. Sci. USA, 94(10):4937-42 (1997).
Hank et al., Activation of human effector cells by a tumor reactive recombinant anti-ganglioside GD2 interleukin-2 fusion protein (ch14. 18-IL2), Clin. Cancer Res., 2(12):1951-9 (1996).
Hawkins et al., Selection of phage antibodies by binding affinity. Mimicking affinity maturation, J. Mol. Biol., 226(3):889-96 (1992).
Hay et al., Bacteriophage cloning and *Escherichia coli* expression of a human IgM Fab, Hum. Antibodies Hybridomas, 3(2):81-5 (1992).
Heng et al., Making cell-permeable antibodies (Transbody) through fusion of protein transduction domains (PTD) with single chain variable fragment (scFv) antibodies: potential advantages over antibodies expressed within the intracellular environment (Intrabody). Med. Hypotheses, 64: 1105-8 (2005).
Hinman et al., Preparation and characterization of monoclonal antibody conjugates of the calicheamicins: a novel and potent family of antitumor antibiotics, Cancer Res., 53(14):3336-42 (1993).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Hoogenboom et al., Multi-subunit proteins on the surface of filamentous phage: methodologies for displaying antibody (Fab) heavy and light chains, Nucleic Acids Res., 19(15):413-7 (1991).
Hosse et al., A new generation of protein display scaffolds for molecular recognition, Protein Sci., 15(1):14-27 (2006).
Hu et al., A chimeric Lym-1/interleukin 2 fusion protein for increasing tumor vascular permeability and enhancing antibody uptake, Cancer Res., 56(21):4998-5004 (1996).
Huse et al., Generation of a large combinatorial library of the immunoglobulin repertoire in phage lambda, Science, 246-1275-81 (1989).
Huston et al., Protein engineering of antibody binding sites: Recovery of specific activity in an anti-digoxin single-chain Fv analogue produced in *Escherichia coll. Proc. Natl. Acad. Sci. USA.* 85:5879-83 (1988).
International Application No. PCT/US2016/020539, International Preliminary Report on Patentability, dated Sep. 5, 2017.
International Application No. PCT/US2016/020539, International Search Report and Written Opinion, dated May 12, 2016.
Ishida et al., Production of human monoclonal and polyclonal antibodies in TransChromo animals, Cloning Stem Cells, 4(1):91-102 (2002).
Jakobovits et al., Analysis of homozygous mutant chimeric mice: deletion of the immunoglobulin heavy-chain joining region blocks B-cell development and antibody production, Proc. Natl. Acad. Sci. USA, 90(6):2551-5 (1993).
Jakobovits et al., Germ-line transmission and expression of a human-derived yeast artificial chromosome, Nature, 362(6417):255-8 (1993).
Jespers et al., Guiding the selection of human antibodies from phage display repertoires to a single epitope of an antigen, Biotechnology (NY), 12(9):899-903 (1994).
Jones et al., Replacing the complementarity-determining regions in a human antibody with those from a mouse, Nature, 321(6069):522-5 (1986).
Kabat et al., Sequences of Proteins of Immunological Interests, National Institutes of Health, Bethesda, Md., (1987 and 1991).
Kettleborough et al., Humanization of a mouse monoclonal antibody by CDR-grafting: the importance of framework residues on loop conformation, Protein Eng., 4(7):773-83 (1991).
Kitamura et al., Insulin receptor knockout mice, Annu. Rev. Physiol., 65:313-32 (2003).
Kohler et al., Continuous cultures of fused cells secreting antibody of predefined specificity, Nature, 256(5517):495-7 (1975).
Kreitman et al., Cytotoxic activities of recombinant immunotoxins composed of Pseudomonas toxin or diphtheria toxin toward lymphocytes from patients with adult T-cell leukemia, Leukemia, 7(4):553-62 (1993).
Kuan et al., Recombinant immunotoxin containing a disulfide-stabilized Fv directed at erbB2 that does not require proteolytic activation, Biochemistry, 35(9):2872-7 (1996).
Lee et al., Microbial cell-surface display, Trends Biotechnol., 21(1):45-52 (2003).
Lee et al., Risk of post-gastric bypass surgery hypoglycemia in nondiabetic individuals: A single center experience, Obesity, 24(6):1342-8 (2016).
Li et al., Comparison of the long-term results of Roux-en-Y gastric bypass and sleeve gastrectomy for morbid obesity: a systematic review and meta-analysis of randomized and nonrandomized trials, Surg. Laparosc. Endosc. Percutan. Tech., 2491):1-11 (2014).
Linardou et al., Deoxyribonuclease I (DNAse I). A novel approach for targeted cancer therapy, Cell Biophys., 25:243-8 (1994).
Lindmark et al., Binding of immunoglobulins to protein A and immunoglobulin levels in mammalian sera. *J. Immunol. Meth.* 62: 1-13 (1983).
Liu et al., Eradication of large colon tumor xenografts by targeted delivery of maytansinoids, Proc. Natl. Acad. Sci. USA, 93(16):8618-23 (1996).
Lode et al., Targeted therapy with a novel enediyene antibiotic calicheamicin $\Theta^1_1$ effectively suppresses growth and dissemination of liver metastases in a syngeneic model of murine neuroblastoma, Cancer Res., 58:2925-8 (1998).
Mandler et al., Immunoconjugates of geldanamycin and anti-HER2 monoclonal antibodies: antiproliferative activity on human breast carcinoma cell lines, J. Natl. Cancer Inst., 92(19):1573-81 (2000).

(56) References Cited

OTHER PUBLICATIONS

Mandler et al., Modifications in synthesis strategy improve the yield and efficacy of geldanamycin-herceptin immunoconjugates, Bioconjug. Chem., 13(4):786-91 (2002).
Mandler et al., Synthesis and evaluation of antiproliferative activity of a geldanamycin-Herceptin immunoconjugate, Bioorg. Med. Chem. Lett., 10(10):1025-8 (2000).
Marks et al., By-passing immunization. Human antibodies from V-gene libraries displayed on phage, J. Mol. Biol., 222(3):581-97 (1991).
Marks et al., By-passing immunization: building high affinity human antibodies by chain shuffling, Biotechnology (NY), 10(7):779-83 (1992).
Marks et al., By-passing immunization: building high affinity human antibodies by chain shuffling, Biotechnology, 10(7):779-83 (1992).
Massey, Catalytic antibodies catching on, Nature, 328:457-8 (1987).
Mather et al., Culture of testicular cells in hormone-supplemented serum-free medium. Annals N.Y. Acad. Sci. 383: 44-68 (1982).
Mather, Establishment and characterization of two distinct mouse testicular epithelial cell lines. Biol. Reprod. 23: 243-251 (1980).
Mathews et al., Change in effective circulating volume during experimental dumping syndrome, Surgery, 48:185-94 (1960).
McCafferty et al., Phage antibodies: filamentous phage displaying antibody variable domains, Nature, 348(6301):552-4 (1990).
Meier et al., Comment to: Patti ME, McMahon G, Mun EC et al. (2005) Severe hypoglycaemia post0gastric bypass requiring partial pancreatectomy: evidence for inappropriate insulin secretion and pancreatic islet hyperplasia. Diabetologia 48:2236-40,: Diabetologia, 49:607-8 (2006).
Meier et al., Hyperinsulinemic hypoglycemia after gastric bypass surgery is not accompanied by islet hyperplasia or increased beta-cell turnover, Diabetes Care, 29(7):1554-9 (2006).
Mhashilkar et al., Inhibition of HIV-1 Tat-mediated LTR transaction and HIV-1 infection by anti-Tat single chain intrabodies. Embo J. 14 (7):1542-51, 1995.
Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Nath et al., Xoma 358, a Novel Treatment for Hyperinsulinemic Hypoglycemia: Safety and Clinical Pharmacology from the First in Human Trial, Abstract, ENDO 2015, San Diego, California (Mar. 7, 2015).
Natsume et al., Improving effector functions of antibodies for cancer treatment: Enhancing ADCC and CDC, Drug Des. Devel. Ther., 3:7-16 (2009).
Neuberger et al., Recombinant antibodies possessing novel effector functions, Nature, 312(5995):604-8 (1984).
Nguyen et al., The specific variable domain of camel heavy-chain antibodies is encoded in the germline, J. Mol. Biol., 275(3):413-8 (1998).
Nicholls et al., Characterization of single-chain antibody (sFv)-toxin fusion proteins produced in vitro in rabbit reticulocyte lysate, J. Biol. Chem., 268(7):5302-8 (1993).
Nicolet et al., Expression of a tumor-reactive antibody-interleukin 2 fusion protein after in vivo particle-mediated gene delivery, Cancer Gene Ther., 2(3):161-70 (1995).
Nuttall et al., Isolation of the new antigen receptor from wobbegong sharks, and use as a scaffold for the display of protein loop libraries, Mol. Immunol., 38(4):313-26 (2001).
Olafsen et al., Characterization of engineered anti-p185HER-2 (scFv-CH3)2 antibody fragments (minibodies) for tumor targeting. Protein Eng. Des. Sel. 17: 315-23 (2004).
Oliyai et al., Prodrugs of peptides and proteins for improved formulation and delivery, Annu. Rev. Pharmacol. Toxicol., 33:521-44 (1993).
Owens et al., Alternative routes of insulin delivery, Diabet. Med., 20(11):886-98 (2003).
Paborsky et al., Mammalian cell transient expression of tissue factor for the production of antigen, Protein Eng., 3(6):547-53 (1990).
Padlan, A possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Pastan et al., Immunotoxin therapy of cancer, Nat. Rev. Cancer, 6(7):559-65 (2006).
Pastan et al., Immunotoxins. Cell, 47: 641-8 (1986).
Patti et al., Severe hypoglycaemia post-gastric bypass requiring partial pancreatectomy: evidence for inappropriate insulin secretion and pancreatic islet hyperplasia, Diabetologia, 48(11):2236-40 (2005).
Patti et al., The rollercoaster of post-bariatric hypoglycaemia, Lancet Diabetes Endocrinol., 4(2):94-6 (2016).
Pluckthun, Antibodies from Escherichia coli (Chapter 11), IN: Rosenberg et al. (eds.), The Pharmacology of Monoclonal Antibodies, Springer-Verlag Berlin Heidelberg (1994).
Poljak, Production and structure of diabodies, Structure, 2(12):1121-3 (1994).
Raju, Terminal sugars of Fc glycans influence antibody effector functions of IgGs, Curr. Opin. Immunol., 20(4):471-8 (2008).
Reichman et al., Single domain antibodies: comparison of camel VH and camelised human VH domains, J. Immunol. Methods, 231:25-38 (1999).
Rothman et al., Antibody-dependent cytotoxicity mediated by natural killer cells is enhanced by castanospermine-induced alterations of IgG glycosylation, Mol. Immunol., 26(12):1113-23 (1989).
Salehi et al., Blockade of glucagon-like peptide 1 receptor corrects postprandial hypoglycemia after gastric bypass, Gastroenterology, 146(3):669-80.e2 (2014).
Sanger et al., DNA sequencing with chain-terminating inhibitors, Proc. Natl. Acad. Sci. USA, 74(12):5463-7 (1977).
Sarmay et al., Mapping and comparison of the interaction sites on the Fc region of IgG responsible for triggering antibody dependent cellular cytotoxicity (ADCC) through different types of human Fc gamma receptor, Mol. Immunol., 29(5):633-9 (1992).
Schmidt et al., A bivalent single-chain antibody-toxin specific for ErbB-2 and the EGF receptor, Int. J. Cancer, 65(4):538-46 (1996).
Schoonjans et al., Fab chains as an efficient heterodimeration scaffold for the production of recombinant bispecific and trispecific antibody derivatives. J. Immunol. 165: 7050-7 (2000).
Sergeeva et al., Display technologies: application for the discovery of drug and gene delivery agents, Adv. Drug Deliv. Rev., 58(15):1622-54 (2006).
Service et al., Hyperinsulinemic hypoglycemia with nesidioblastosis after gastric-bypass surgery, N. Engl. J. Med., 353(3):249-54 (2005).
Service, Classification of hypoglycemic disorders, Endocrinol. Metab. Clin. North America, 28(3):501-17 (1999).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276(9):6591-604 (2001).
Shields et al., Lack of fucose on human IgG1 N-linked oligosaccharide improves binding to human Fcgamma RIII and antibody-dependent cellular toxicity, J. Biol. Chem., 277(30):26733-40 (2002).
Shih et al., A fluorouridine-anti-CEA immunoconjugate is therapeutically effective in a human colonic cancer xenograft model, Int. J. Cancer, 46(6):1101-6 (1990).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shopes, A genetically engineered human IgG mutant with enhanced cytolytic activity, J. Immunol., 148(9):2918-22 (1992).
Silverstein et al., Care of children and adolescents with type 1 diabetes: a statement of the American Diabetes Association, Diabetes Care, 28(1):186-212 (2005).
Singh et al., Hypoglycemia after gastric bypass surgery, Diabetes Spectrum, 25:217-21 (2012).
Skerra, Alternative non-antibody scaffolds for molecular recognition, Curr. Opin. Biotechnol., 18(4):295-304 (2007).

(56) References Cited

OTHER PUBLICATIONS

Steplewski et al., Biological activity of human-mouse IgG1, IgG2, IgG3, and IgG4 chimeric monoclonal antibodies with antitumor specificity, Proc. Natl. Acad. Sci. USA, 85(13):4852-6 (1988).

Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).

Stevenson et al., A chimeric antibody with dual Fc regions (bisFabFc) prepared by manipulations at the IgG hinge, Anticancer Drug Des., 3(4):219-30 (1989).

Studnicka et al., Human-engineered monoclonal antibodies retain full specific binding activity by preserving non-CDR complementarity-modulating residues, Protein Eng., 7(6):805-14 (1994).

Thompson et al., An anti-CD3 single-chain immunotoxin with a truncated diphtheria toxin avoids inhibition by pre-existing antibodies in human blood, J. Biol. Chem., 270(47):28037-41 (1995).

Umana et al., Engineered glycoforms of an antineuroblastoma IgG1 with optimized antibody-dependent cellular cytotoxic activity, Nat. Biotechnol., 17(2):176-80 (1999).

Urlaub et al., Isolation of Chinese hamster cell mutants deficient in dihydrofolate reductase activity. *Proc. Natl. Acad. Sci. USA*. 77: 4216-20 (1980).

Vallera et al., Anti-graft-versus-host disease effect of DT390-anti-CD3sFv, a single-chain Fv fusion immunotoxin specifically targeting the CD3 epsilon moiety of the T-cell receptor, Blood, 88(6):2342-53 (1996).

Verhoeyen et al., Reshaping human antibodies: grafting an antilysozyme activity, Science, 239:1534-6 (1988).

Wada et al., New twist on neuronal insulin receptor signaling in health, disease, and therapeutics, J. Pharmacol. Sci., 99(2):128-43 (2005).

Wang et al., Abstracts of the 209th ACS National Meeting, Anaheim, Calif., Apr. 2-6, 1995, Part 1, BIOT005.

Ward et al., Binding activities of a repertoire of single immunoglobulin variable domains secreted from *Escherichia coli*, Nature, 341(6242):544-6 (1989).

Ward et al., Ligand-induced activation of the insulin receptor: a multi-step process involving structural changes in both the ligand and the receptor, Bioessays, 31(4):422-34 (2009).

Ward et al., Structural insights into ligand-induced activation of the insulin receptor, Acta Physiol. (Oxf.), 192(1):3-9 (2008).

Watkins, Screening of phage-expressed antibody libraries by capture lift. *Methods in Molecular Biology, Antibody Phage Display: Methods and Protocols*. 178: 187-193.

Weinstein et al., Insulin analogues display IGF-I-like mitogenic and anti-apoptotic activities in cultured cancer cells, Diabetes Metab. Res. Rev., 25(1):41-9 (2009).

Wels et al., EGF receptor and p185erbB-2-specific single-chain antibody toxins differ in their cell-killing activity on tumor cells expressing both receptor proteins, Int. J. Cancer, 60(1):137-44 (1995).

Wheeler et al. Intrabody-based strategies for inhibition of vascular endothelial growth factor receptor-2: effects on apoptosis, cell growth, and angiogenesis. *Faseb. J.* 17: 1733-5 (2003).

Willems et al., Optimizing expression and purification from cell culture medium of trispecific recombinant antibody derivatives, J. Chromatogr. B Analyt. Technol. Biomed. Life Sci., 786(12):161-76 (2003).

Winter et al., Making antibodies by phage display technology, Annu. Rev. Immunol., 12:433-55 (1994).

Wittrup, Protein engineering by cell-surface display, Curr. Opin. Biotechnol., 12(4):395-9 (2001).

Wolff et al., Monoclonal antibody homodimers: enhanced antitumor activity in nude mice, Cancer Res., 53(11):2560-5 (1993).

Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).

Yang et al., A genetically engineered fusion protein M4/TNF with increased bifunctional activity refolded in the presence of protein disulfide isomerase, Hum. Antibodies Hybridomas, 6(4):129-36 (1995).

Yorifuji, Congenital hyperinsulinism: current status and future perspectives, Ann. Pediatr. Endocrinol. Metab., 19(2):57-68 (2014).

Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).

\* cited by examiner

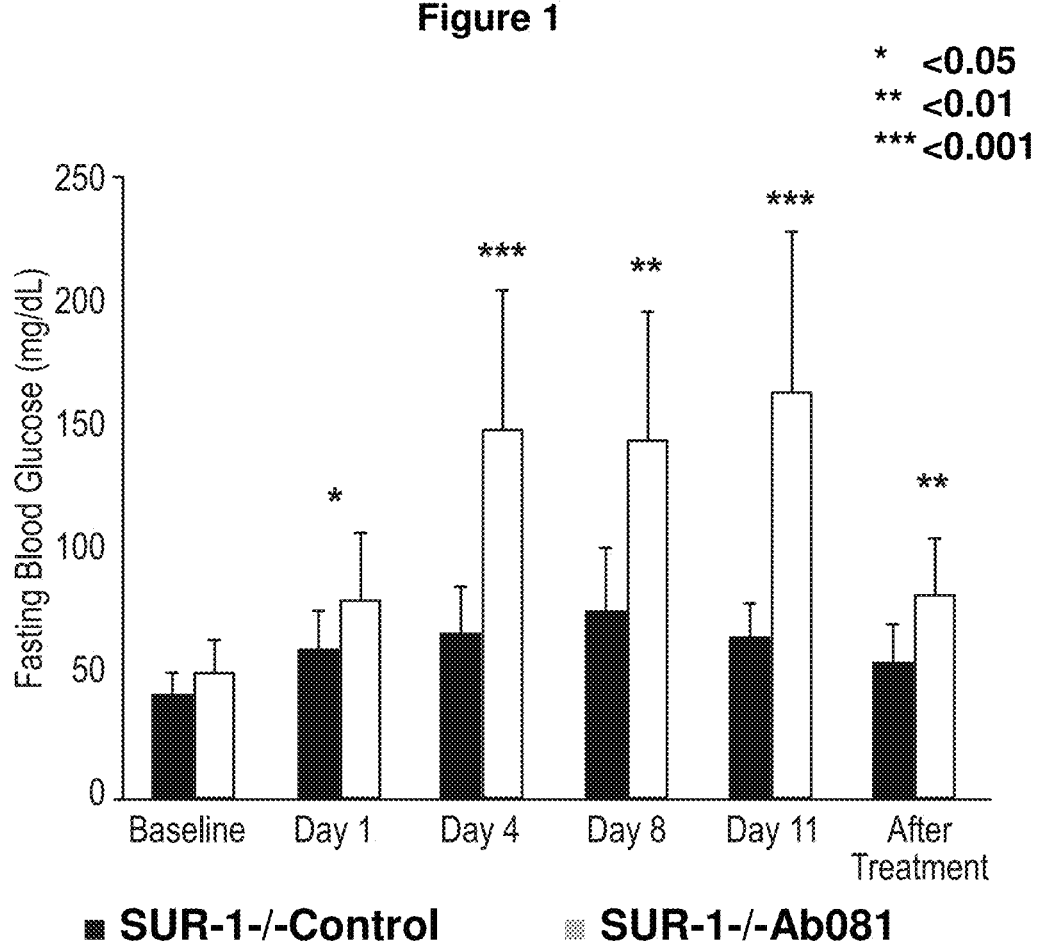

Figure 7

Heavy chain

| Ab # | H-FR1 | H-CDR1 | H-FR2 | H-CDR2 | H-FR3 | H-CDR3 | H-FR4 | SEQ ID NO: |
|---|---|---|---|---|---|---|---|---|
| Ab081 | EVQLVETGGGVVQPGRSLRLSCAAS | GFTFSSYA | MHWVRQAPGKGLEWVAV | ISYDGSNK | YYADSVKGRFTISRDNSKNTLYLQMNSLRAEDTAVYYC | ARHEWGFGMDV | WGQGTTVTVSS | 1 |
| Ab061 | QMQLVQSGAEVKKTGESLKISCQGY | GYRFTDNW | IGWVRQMPGRGLEWMGI | IYPGDSET | RYSPSFQGQVTISADKSISTAYLEWSSLKASDTAMYYC | ARHAPLAVAGMALGD | WGQGTLVTVSS | 2 |
| Ab070 | EVQLVQSGAEVKKPGESLKISCKGS | GYSFTSYW | IGWVRQMPGKGLEWMGI | IYPGDSDT | RYSPSFQGQVTISADKSISTSYLQWSSLRASDTAMYYC | ARLGSGWYGNDY | WGQGTLVTVSS | 3 |
| Ab020 | QVQLQQSEAELVKPGASVKISCKAS | GYTFSSYW | MNWVKQRPGKGLEWIGQ | IYPGDGDT--- | NYNVKFKGKATLTADKSSGTAYMQLSSLTSEDSAVYFC | ARGVSGYGAMDY | WGQGTSVTVSS | 4 |
| Ab052 | EVQLVQSGAEVKKPGESLKISCKGS | GYRFTSYW | IGWVRQMPGRGLEWMGI | IYPGDSDT | RYSPSFQGQVTISVDKSISTAYLQWSSLKASDTAMYYC | ATHHASGRGLDP | WGQGTLVTVSS | 5 |

Light chain

| Ab # | L-FR1 | L-CDR1 | L-FR2 | L-CDR2 | L-FR3 | L-CDR3 | L-FR4 | SEQ ID NO: |
|---|---|---|---|---|---|---|---|---|
| Ab081 | DVVMTQSPLSLSVTLGQPASISCRSS | LSLVYGDENTY | LNWFQQRPGQSPRRLLY | KVS | DRDSGVPDRFSGSGSGTDFTLKISRVEADDVGVYYC | MQGTHWP | YTFGQGTKLEIK | 6 |
| Ab061 | QTVVTQEPSFSVSPGGTVTLTCGLS | SGSVSTGYS | PGWYQQTPGQAPRTLVY | NTN | TRSSGVPDRFSGSILGNKAALTITGAQADDESDYYC | ALYMGSGTY | VFGGGTKLTVL | 7 |
| Ab070 | SSELTQDPAVSVALGQTVRITCQGD | SLRSYY | TSWYQQKPGQAPVLVIF | GKN | NRPSGIPDRFSGSSGNTASLTITGAQAEDEADYYC | NSRDSSGNYA | VFGGGTQLTVL | 8 |
| Ab020 | DLVLTQSPASLAVSLGQRATISCRAS | KSVSTSGYSY | IHWYQQRPGQPPKLLIY | LAS | NLESGVPARFSGSGSGTDFTLNIHPVEEEDAATYYC | -QHNREL | RTFGGGTKLEIKR | 9 |
| Ab052 | QAMLTQPASLSASPGASASLTCTLR | SGINVVAYN | IYWYRQKSGSPPQSVLR | YKSDSDS | ERDSGVPSRFSGSKDVSANAGILLISGLQSEDEADYYC | LIWHNSAW | VFGGGTQLTVL | 10 |

US 10,711,067 B2

TREATMENT OF POST-PRANDIAL HYPERINSULINEMIA AND HYPOGLYCEMIA AFTER BARIATRIC SURGERY

CROSS REFERENCE TO RELATED APPLICATIONS

This application claims the priority benefit of U.S. Provisional Patent Application Nos. 62/127,788, filed Mar. 3, 2015 and 62/288,955, filed Jan. 29, 2016, hereby incorporated by reference in their entirety.

FIELD OF THE INVENTION

The present disclosure, relates, in general, to the use of a negative modulator antibody specific for the insulin receptor that modulates the binding of insulin to the insulin receptor in the treatment of hyperinsulinemia and hypoglycemia that occurs after eating in patients who have undergone bariatric, or gastric bypass, surgery.

BACKGROUND OF THE INVENTION

Insulin is the major hormone for lowering blood glucose levels. Abnormal increases in insulin secretion can lead to profound hypoglycemia or low blood sugar, a state that may result in significant morbidities including epilepsy and cerebral damage. A number of rare medical conditions feature non-drug-induced, endogenous hyperinsulinemic hypoglycemia, i.e., low blood glucose caused by the body's excessive production of insulin. These conditions include congenital hyperinsulinism, insulinoma, and hyperinsulinemic hypoglycemia following gastric bypass surgery.

Congenital hyperinsulinism (CHI) comprises a group of genetic disorders that are characterized by recurrent episodes of hyperinsulinemic hypoglycemias due to unregulated secretion of insulin by the pancreatic β-cells [Arnoux J., et al. Orphanet Journal of Rare Diseases 6:63 (2011); Yorifuji T., Ann Pediatr Endocrinol Metab. 19:57-68 (2014)]. CHI is the most common cause of hyperinsulinemic hypoglycemia in neonatal, infant and childhood periods and is usually diagnosed within the first two years of life. Histopathologically, CHI can present in either diffuse or focal forms. In the diffuse form all pancreatic β-cells are affected, whereas in focal forms lesions of abnormal β-cells are (usually) restricted to small areas of the pancreas. The most common known causes of CHI are loss-of-function mutations in the genes encoding for SUR1 and Kir6.2, subunits of the ATP-sensitive potassium channel (KATP channel), involved in the secretion of insulin in pancreatic β-cells.

Post-prandial hypoglycemia (PPH) has recently been observed as a side effect or complication of gastric bypass surgery (Singh et al., Diabetes Spectrum 25: 217-221, 2012; Patti et al., Diabetologia 48:2236-2240, 2005; Service et al. N Engl J Med 353:249-254, 2005), including after the common procedure of Roux-en-Y gastric bypass (RYGB). A commonly observed side effect of gastric bypass surgery is "dumping" which is consequence of the ingestion of simple sugars and rapid emptying of food into the small intestine. This is often characterized by vasomotor symptoms (flushing, tachycardia), abdominal pain, and diarrhea (Singh et al., Diabetes Spectrum 25: 217-221, 2012; Mathews et al., Surgery 48:185-194, 1960). Late dumping can occur up to a few hours after eating and results from insulin response to hyperglycemia resulting from rapid absorption of simple sugars from the proximal small intestine. In contrast to dumping, which is noted soon after surgery and improves with time, hyperinsulinemic hypoglycemia presents several months to years (usually around 1 year, up to 3 years) after gastric bypass surgery. This syndrome is differentiated from dumping by onset of severe postprandial neuroglycopenia, which is typically absent in dumping, as well as pancreatic nesidioblastosis (islet cell enlargement, β-cells budding from ductal epithelium, and islets in apposition to ducts). Unlike with dumping, nutrition modification does not alleviate the symptoms of post-prandial hypoglycemia (PPH).

SUMMARY OF THE INVENTION

The present disclosure relates to use of negative modulator antibodies against the insulin receptor to treat patients that have post-prandial hypoglycemia that occurs after gastric bypass surgery.

In various embodiments, the disclosure provides a method of treating post-prandial hypoglycemia following bariatric surgery, comprising administering to a subject in need thereof an antibody that is a negative modulator of insulin binding to the insulin receptor and/or insulin action at the insulin receptor in an amount effective to ameliorate one or more symptoms of post-prandial hypoglycemia.

In various embodiments, the disclosure also provides a method of preventing post-prandial hypoglycemia following bariatric surgery, comprising administering to a subject in need thereof an antibody that is a negative modulator of insulin binding to the insulin receptor and/or insulin action at the insulin receptor in an amount effective to prevent post-prandial hypoglycemia It is contemplated that a subject at risk for post-prandial hypoglycemia after bariatric surgery is administered an antibody as described herein in order to prevent onset of post-prandial hypoglycemia. In various embodiments, an at-risk subject is a subject is typically at or after 1 year post bariatric surgery, has shown resistance to other treatments for hypoglycemia, presents with demonstrable provocable symptoms of hypoglycemia and/or has demonstrated insulin sensitivity.

In various embodiments, the subject has a blood glucose level of less than 70 mg/dL prior to administration of an antibody described herein. In various embodiments, the subject has a blood glucose level of less than 55 mg/dL prior to administration.

In various embodiments, at risk subjects are subjects who know that a certain meal provokes hypoglycemia, for example, a meal is given and a mixed meal test (MMT) is performed and an at-risk subject will often have provocation of hypoglycemia.

Administration to an at-risk patients before or at the beginning of symptoms can reduce need for alternate or current standard of care treatments, reduce the need for a pancreatectomy and reduce the number of doctor visits for the treated subject.

In various embodiments, the antibody binds to (i) insulin receptor or (ii) a complex comprising insulin and insulin receptor, or both (i) and (ii), with an equilibrium dissociation constant $K_D$ of $10^{-5}$ M or less that is capable of weakening the binding affinity between insulin and insulin receptor by at least about 3-fold, optionally up to 1000-fold. In certain embodiments, the antibody is capable of weakening the binding affinity between said insulin and insulin receptor by about 3-fold to 500-fold. In various embodiments, the antibody increases the $EC_{50}$ of insulin signaling activity by about 2-fold to 1000-fold, optionally in a pAKT assay.

In one embodiment, antibody refers to an antibody or fragment thereof, or a polypeptide comprising an antigen binding domain of an antibody. Exemplary antibodies or antibody fragments include polyclonal antibodies, monoclonal antibodies, chimeric antibodies, humanized antibodies, human antibodies, multispecific antibodies, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences. In one embodiment, the antibody is a monoclonal antibody. In a related embodiment, the antibody is a human antibody.

In exemplary embodiments, the methods herein contemplate use of:

a monoclonal antibody that retains any one, two, three, four, five, or six of HCDR1, HCDR2, HCDR3, LCDR1, LCDR2, or LCDR3 of any one of SEQ ID NOs: 11-25 and SEQ ID NOs: 26-40, respectively, optionally including one or two mutations in such CDR(s), e.g., a conservative or non-conservative substitution;

a monoclonal antibody that retains all of HCDR1, HCDR2, HCDR3, or the heavy chain variable region of any one of SEQ ID NOs: 11-25 or SEQ ID NO: 1-5, respectively, optionally including one or two mutations in any of such CDR(s), optionally further comprising any suitable heavy chain constant region, e.g., IgG1, IgG2, IgG3, IgG4, IgM, IgA1, IgA2, or IgE or hybrid thereof;

a monoclonal antibody that retains all of LCDR1, LCDR2, LCDR3, or the light chain variable region of any one SEQ ID NOs: 26-40 or SEQ ID NO: 6-10, optionally including one or two mutations in any of such CDR(s), optionally further comprising to any suitable light chain constant region, e.g. a kappa or lambda light chain constant region;

a purified preparation of a monoclonal antibody, comprising the light chain variable region and heavy chain variable regions as set forth in SEQ ID NOs: 1-10;

a monoclonal antibody that binds to the same linear or three-dimensional epitope of INSR as an antibody comprising a variable region set out in SEQ ID NO: 1-10, e.g., as determined through X-ray crystallography or other biophysical or biochemical techniques such as deuterium exchange mass spectrometry, alanine scanning and peptide fragment ELISA;

a monoclonal antibody that competes with an antibody comprising a variable region set out in SEQ ID NO: 1-10, optionally paired as in Table 1, for binding to human INSR by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, all three heavy chain CDRs, or all six CDRs of an antibody comprising a variable region set out in SEQ ID NO: 11-40. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g., heavy or light) of any of the antibodies described herein, e.g. to form a suitable heavy or light chain variable region.

In another aspect, the disclosure provides for use of variants or derivatives of the antibodies described herein. For example, in one embodiment the antibody is labeled with a detectable moiety as described herein. In a further embodiment, the antibody is conjugated to a hydrophobic moiety described herein.

Variants of the antibodies include antibodies having a mutation or alteration in an amino acid sequence provided herein, including an amino acid insertion, deletion or substitution, e.g., a conservative or non-conservative substitution.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NO: 1-5 and/or an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NO: 6-10, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

It is contemplated that the antibodies used herein may have one, or two or more amino acid substitutions in the CDR regions of the antibody, e.g. conservative substitutions.

In various embodiments, the antibody used in the methods comprises a heavy chain variable region selected from the group consisting of SEQ ID NOs: 1-5 and a light chain variable region selected from the group consisting of SEQ ID NOs: 6-10. In various embodiments, the variable heavy chain is set out in SEQ ID NOs: 1-3 and the variable light chain is set out in SEQ ID NOs: 6-8.

In various embodiments, the antibody comprises three heavy chain CDRs set out in SEQ ID NOs: 11-13, 14-16 or 17-19 and three light chain CDRs set out in SEQ ID NOs: 26-28, 29-31 or 32-34.

In one embodiment, the variable heavy chain is set out in SEQ ID NO: 1 and the variable light chain is set out in SEQ ID NO: 6. In another embodiment, the antibody comprises three heavy chain CDRs set out in SEQ ID NO: 11-13 and three light chain CDRs set out in SEQ ID NO: 26-28.

In various embodiments, the antibody is a monoclonal antibody. In various embodiments, the antibody is a human antibody.

In various embodiments, the antibody is conjugated to a hydrophobic moiety.

In various embodiments, the antibody is in a pharmaceutical composition.

In various embodiments, the disclosure contemplates a method of preparing a sterile pharmaceutical composition, comprising adding a sterile pharmaceutically acceptable diluent to an antibody contemplated herein. Optionally small amounts of a preservative such as a bactericidal or bacteriostatic agent are also included in the composition. Also contemplated is a sterile composition comprising an antibody described herein and a sterile pharmaceutically acceptable diluent.

In various embodiments, the antibody is administered at a dose of from 0.1 to 25 mg/kg. In various embodiments, the antibody is administered at a dose of from 0.3 to 9 mg/kg. Additional doses contemplated include from about 0.3 to 15 mg/kg, or from about 1 to 6 mg/kg. Exemplary doses include, 0.1 mg/kg, 0.3 mg/kg, 0.5 mg/kg 1 mg/kg, 0.75 mg/kg, 1.0 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg. Other doses include 1 mg/day, 2.5 mg/day, 5 mg/day, 10 mg/day, 20 mg/day, 25 mg/day, 50 mg/day, 75 mg/day, 100 mg/day, 150 mg/day, 200 mg/day, 250 mg/day, 500 mg/day or 1000 mg/day.

In various embodiments, the antibody is administered once per week, once every two weeks, or once a month. Also contemplated is administration once daily, as well as continuous infusion, optionally low dose continuous infusion. In various embodiments, the half-life of the antibody is from approximately 14 to 25 days. Additional doses are methods for administration are discussed in more detail in the Detailed Description.

In various embodiments, the antibody is administered intravenously, intraarterially, intraperitoneally, intramuscularly, intradermally, subcutaneously, orally or by continuous infusion. In various embodiments the antibody is administered via continuous infusion pump or depot.

In various embodiments, the administration takes place during a fasting regimen.

In various embodiments, the antibody reduces hyperinsulinemia or excess insulin signaling.

In various embodiments, the antibody results in increased circulating insulin levels, probably by reducing insulin receptor-mediated insulin clearance, and yet wherein the elevated insulin is not acting to lower glucose (e.g., by inhibiting insulin signaling).

In various embodiments, the administration increases post-prandial blood glucose in the subject by 1.5 to 10 fold or more, or 10 to 40% or more. In various embodiments, the administration increases post-prandial blood glucose in the subject by approximately 10 mg/dL or more. In various embodiments, the administration increases blood glucose back into the normal range.

In various embodiments, the administration reduces the frequency of hyperglycemic events (blood glucose>200 mg/dL). In various embodiments, the administration reduces the frequency of hypoglycemic events (blood glucose<60 mg/dL). Additional parameters monitored for improvement toward the normal range include, but are not limited to, insulin levels, c-peptide levels, ketone levels, and free fatty acid levels.

In various embodiments, the administration induces insulin resistance. In various embodiments, insulin resistance is measured by meal tolerance test, insulin tolerance test fasting HOMA-IR assay and/or oral glucose tolerance test.

It is contemplated that one or more of the parameters or outcome measures described herein is improved by at least about 10%, 20%, 30%, 40%, 50%, 60%, 70% or more, or by at least about 1, 1.5, 2, 2.5, 3, 4, 5, 6, 7, 8, 9, 10-fold or more.

In various embodiments, the patient is also on a restricted diet regimen.

In various embodiments, the method further comprises administering a second agent. In various embodiments, the second agent is acarbose, octreotide, verapamil or diazoxide.

In various embodiments, administration of the antibody removes the need for nasogastric food control or strict/challenging diet control. In various embodiments, administration of the antibody reduces the need for or amount of hyperinsulinemia therapeutic administered, e.g., somatostatin analogs, diazoxide, glucocorticoids, and reduces tolerability/safety issues associated with the hyperinsulinemia therapeutic.

In various embodiments, administration of the antibody according to the methods herein provides an additive or synergistic benefit with a hyperinsulinemia therapeutic agent, thereby reducing dosage amounts of the hyperinsulinemia therapeutic agent and providing a safer profile of these agents.

In various embodiments the administration reduces or ameliorates symptoms of post-prandial hypoglycemia selected from the group consisting of pancreatic nesidioblastosis, islet cell enlargement, islet cell hyperplasia, β cell budding, tachycardia, diaphoresis, and flushing.

Use of any of the foregoing antibodies or polypeptides described herein that modulate the insulin-INSR signaling interaction in preparation of a medicament for treatment of any of the disorders described herein is also contemplated. Syringes, e.g., single use or pre-filled syringes, sterile sealed containers, e.g. vials, bottle, vessel, and/or kits or packages comprising any of the foregoing antibodies or polypeptides, optionally with suitable instructions for use, are also contemplated.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Similarly, where a method describes using or identifying polypeptide binding agents, such as antibodies, characterized by certain features, polypeptide binding agents characterized by those features are also contemplated by the disclosure. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE DRAWINGS

FIG. 1 shows Ab081 increased fasting blood glucose from a hypoglycemic level to normoglycemic levels or above in Sur1 knockout mice.

FIG. 7 sets out the amino acid sequences of antibodies described herein.

DETAILED DESCRIPTION

Figure 2A:
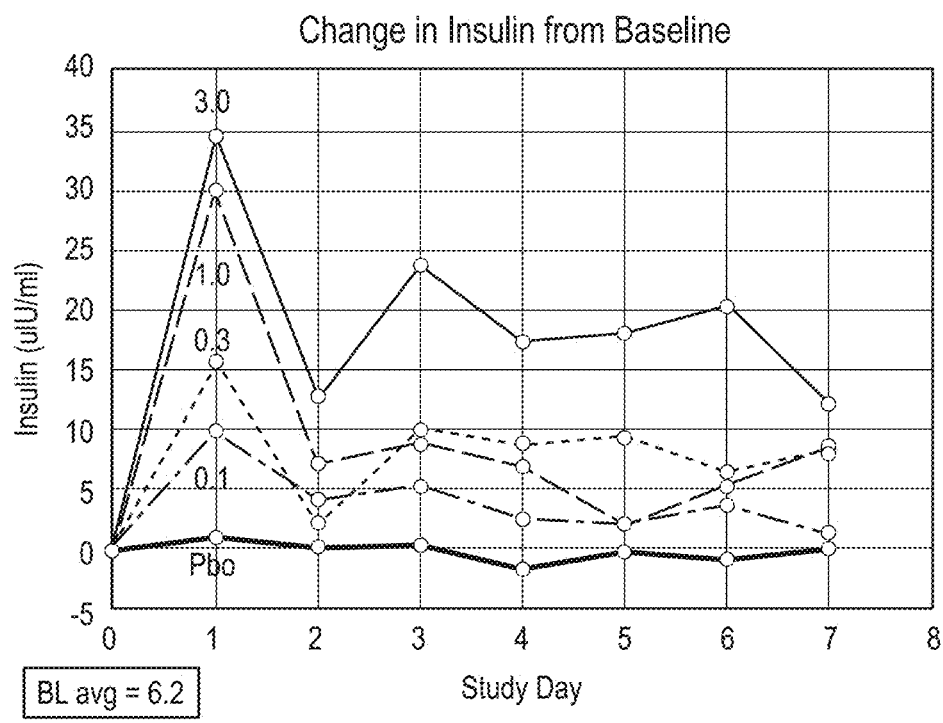
FIGS. 2A and 2B shows a dose-dependent AM fasting serum insulin elevation (FIG. 2A) without significant C-peptide modulation (FIG. 2B).

The disclosure provides use of antibodies specific for the insulin receptor (INSR) or the insulin receptor-insulin complex and uses thereof in the treatment of a disorders related to aberrant glucose levels, e.g. hypoglycemia, more specifically post-prandial hypoglycemia. The antibodies contemplated herein induce a negative effect on the cellular response to insulin by altering the kinetic rate constants for assembly and dissociation of INSR-INS signaling complex components or by other mechanisms including altering the structural state of the signaling complex, e.g., by binding to a transition state and accelerating the activation of signaling.

Not to be bound by theory but it is contemplated that modulation of a signaling complex can result in a decrease in sensitivity to signal input and concomitant decreases in signal transduction. Administration of a negative modulator antibody decreases the sensitivity of the cellular pathway and/or absolute levels of the cellular response.

Definitions

The term "compound" refers to any chemical compound, organic or inorganic, endogenous or exogenous, including, without limitation, polypeptides, proteins, peptides, small molecules, nucleic acids (e.g. DNA and RNA), carbohydrates, lipids, fatty acids, steroids, purines, pyrimidines, peptidomimetics, polyketides and derivatives, structural analogs or combinations thereof. "Endogenous" means naturally occurring in a mammal, while "exogenous" means not naturally occurring in the mammal, e.g., an administered foreign compound, whether naturally occurring or a man-made compound.

The term "polypeptide binding agent" refers to a polypeptide that is capable of specifically binding an antigen, e.g. a target or its signaling partner, or that is capable of binding an antigen with a measurable binding affinity. Examples of polypeptide binding agents include antibodies, peptibodies, polypeptides and peptides, optionally conjugated to other peptide moieties or non-peptidic moieties. Antigens to which a polypeptide binding agent may bind include any proteinaceous or non-proteinaceous molecule that is capable of eliciting an antibody response, or that is capable of binding to a polypeptide binding agent with detectable binding affinity greater than non-specific binding. The antigen to which a modulating polypeptide binding agent binds may include a target, a signaling partner of a target, and/or a complex comprising the target and its signaling partner.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of an antigen to which it binds. Accordingly, a "neutralizing" antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Heavy chain variable region" as used herein refers to the region of the antibody molecule comprising at least one complementarity determining region (CDR) of said antibody heavy chain variable domain. The heavy chain variable region may contain one, two, or three CDR of said antibody heavy chain.

"Light chain variable region" as used herein refers to the region of an antibody molecule, comprising at least one complementarity determining region (CDR) of said antibody light chain variable domain. The light chain variable region may contain one, two, or three CDR of said antibody light chain, which may be either a kappa or lambda light chain depending on the antibody.

As used herein, an antibody that "specifically binds" is "antigen specific", is "specific for" antigen target or is "immunoreactive" with an antigen refers to an antibody or polypeptide binding agent used herein that binds an antigen with greater affinity than other antigens of similar sequence. In one aspect, the polypeptide binding agents, or fragments, variants, or derivatives thereof, will bind with a greater affinity to human antigen as compared to its binding affinity to similar antigens of other, i.e., non-human, species, but polypeptide binding agents that recognize and bind orthologs of the target are within the scope of the methods.

For example, a polypeptide binding agent that is an antibody or fragment thereof "specific for" its cognate antigen indicates that the variable regions of the antibodies recognize and bind the desired antigen with a detectable preference (e.g., where the desired antigen is a polypeptide, the variable regions of the antibodies are able to distinguish the antigen polypeptide from other known polypeptides of the same family, by virtue of measurable differences in binding affinity, despite the possible existence of localized sequence identity, homology, or similarity between family members). It will be understood that specific antibodies may also interact with other proteins (for example, S. aureus protein A or other antibodies in ELISA techniques) through interactions with sequences outside the variable region of the antibodies, and in particular, in the constant region of the molecule. Screening assays to determine binding specificity of a polypeptide binding agent, e.g. antibody, for use in the methods herein are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the methods can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous.

The term "derivative" when used in connection with polypeptide binding agents and polypeptides used herein refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the starting material.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to another labeled nucleic acid molecule. The detectable moiety often generates a measurable signal, such as a radioactive, chromogenic, or fluorescent signal, that can be used to quantitate the amount of bound detectable moiety in a sample.

"Peptides" or "oligopeptides" are short amino acid sequences, typically between 3 and 100 amino acid residues in length and encompass naturally occurring amino acid residues and non-naturally occurring analogs of residues which may be used singly or in combination with naturally occurring amino acid residues in order to give the peptide a particular conformational specificity or a particular biological activity, such as resistance to proteolysis. Peptides include repeats of peptide sequences and may include 2, 3, 4, 5, 6, 7, 8, 9, 10 or more copies of an amino acid sequence arranged head-to-tail or head-to-head. Peptides may be conjugated to non-peptidic moieties. Peptides include dimers, trimers or higher order multimers, e.g. formed through conjugation to other polymeric or non-polymeric moieties, such as PEG.

"Polypeptides" are longer amino acid sequences, typically 100 or more amino acid residues in length, and encompass naturally occurring amino acid residues and non-naturally occurring analogs of residues which may be used singly or in combination with naturally occurring amino acid residues in order to give the polypeptide a particular conformational specificity or a particular biological activity, such as resistance to proteolysis.

As used herein, a "peptibody" is a fusion polypeptide comprising one or more peptides fused to all or a portion of an immunoglobulin (Ig) constant region. See, e.g., U.S. Pat. No. 6,660,843. The peptide may be any naturally occurring or recombinantly prepared or chemically synthesized peptide that binds to the antigen. The peptide may be repeated and may include 2, 3, 4, 5, 6, 7, 8, 9, 10 or more copies of an amino acid sequence arranged head-to-tail or head-to-head. The portion of the Ig constant region may include at least one constant region domain (e.g., CH1, CH2, CH3, and/or CH4), multiple domains (e.g., CH2 with CH3), multiple copies of domains (e.g., CH2-CH2), any fragment of a constant domain that retains the desired activity, e.g. the salvage receptor epitope responsible for the prolonged half-life of immunoglobulins in circulation, or any combinations thereof.

A "small" molecule or "small" organic molecule is defined herein as a non-polymeric organic chemical compound having a molecular weight of about 1000 Daltons or less.

As used herein, a "signaling complex" is an assembly of proteins and/or endogenous or exogenous compounds that mediate the transduction of a cellular signal. Examples of a signaling complex include, but are not limited to, a ligand bound to a membrane bound receptor, an enzyme bound to a substrate or any cellular molecules that associate to propagate biochemical reactions that are involved in a signal cascade. Signaling complexes can also include coreceptors, cofactors, scaffold proteins, allosteric modulators and numerous other types of proteins and molecules that are involved in cellular signal transduction. Signaling complexes can be formed transiently or can be long lived. The molecular constituents or components of a signaling complex can vary over time and can be dependent on activation state of each component and the cellular environment. Signaling complexes can undergo chemical modification and regulation that can induce a spectrum of effects on the complex including subtle changes in transduction activity, complete inactivation and constitutive activation or both positive and negative modulation.

The term "therapeutically effective amount" is used herein to indicate the amount of target-specific composition that is effective to ameliorate or lessen symptoms or signs of disease associated with abnormal (e.g. abnormally high or abnormally low) signaling of the signaling complex.

As used herein "binding" is the physical association between two or more distinct molecular entities that results from a specific network of non-covalent interactions consisting of one or more of the weak forces including hydrogen bonds, Van der Waals, ion-dipole and hydrophobic interactions and the strong force ionic bonds. The level or degree of binding may be measured in terms of affinity. Affinity is a measure of the strength of the binding interaction between two or more distinct molecular entities that can be defined by equilibrium binding constants or kinetic binding rate parameters. Examples of suitable constants or parameters and their measurement units are well known in the art and include but are not limited to equilibrium association constant ($K_A$), e.g. about $10^5 M^{-1}$ or higher, about $10^6 M^{-1}$ or higher, about $10^7 M^{-1}$ or higher, about $10^8 M^{-1}$ or higher, about $10^9 M^{-1}$ or higher, about $10^{10} M^{-1}$ or higher, about $10^{11} M^{-1}$ or higher or about $10^{12} M^{-1}$ or higher; equilibrium dissociation constant ($K_D$), e.g., about $10^{-5} M$ or less, or about $10^{-6} M$ or less, or about $10^{-7} M$ or less, or about $10^{-8} M$ or less, or about $10^{-9} M$ or less, or about $10^{-10} M$ or less, or about $10^{-11} M$ or less, or about $10^{-12} M$ or less; on-rate (e.g., $sec^{-1}$, $mol^{-1}$) and off-rate (e.g., $sec^{-1}$)). In the case of $K_A$, higher values mean "stronger" or "strengthened" binding affinity while in the case of $K_D$, lower values mean "stronger" or "strengthened" binding affinity. As used herein, a "strengthened" binding rate parameter means increased residency time, stronger association or weaker dissociation. As used herein, a "weakened" binding rate parameter means decreased residency time, weaker association or stronger dissociation. In the case of on-rate, higher values mean faster or more frequent association and thus generally result in strengthened binding affinity. In the case of off-rate, lower values generally mean slower dissociation and thus generally result in stronger binding affinity. However, it is the ratio of the on-rate and off-rate that indicates binding affinity, as explained in further detail later.

Affinity between two compounds, e.g., between an antibody and an antigen, or between first and second components of a signaling complex, may be measured directly or indirectly. Indirect measurement of affinity may be performed using surrogate properties that are indicative of, and/or proportional to, affinity. Such surrogate properties include: the quantity or level of binding of a first component to a second component of a signaling complex, or a biophysical characteristic of the first component or the second component that is predictive of or correlated to the apparent binding affinity of the first component for the second component. Specific examples include measuring the quantity or level of binding of first component to a second component at a subsaturating concentration of either the first or the second component. Other biophysical characteristics that can be measured include, but are not limited to, the net molecular charge, rotational activity, diffusion rate, melting temperature, electrostatic steering, or conformation of one or both of the first and second components. Yet other biophysical characteristics that can be measured include determining stability of a binding interaction to the impact of varying temperature, pH, or ionic strength.

Measured affinity is dependent on the exact conditions used to make the measurement including, among many other factors, concentration of binding components, assay setup, valence of binding components, buffer composition, pH, ionic strength and temperature as well as additional components added to the binding reaction such as allosteric modulators and regulators. Quantitative and qualitative methods may be used to measure both the absolute and relative strength of binding interactions.

Apparent affinity is a measure of the strength of the binding interaction between two or more distinct molecular entities under conditions where the affinity is altered by conditions or components in the binding reaction such as allosteric modulators, inhibitors, binding component valence etc.

As used herein a "subsaturating concentration" is a concentration of one or more components in a binding reaction that is significantly below the binding affinity $K_D$ and/or a concentration of one component in a binding reaction that is less than is required to occupy all of the binding sites of the other component(s). Under subsaturating conditions a significant percentage of one of the binding components in the binding reaction has available binding sites.

A receptor "antagonist" is a type of receptor ligand or drug that does not provoke a biological response itself upon binding to a receptor, but blocks or dampens agonist-mediated responses. Antagonists may have affinity but no efficacy for their cognate receptors, and binding will disrupt the interaction and inhibit the function of an agonist or inverse agonist at receptors. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding. The majority of antagonists achieve their potency by competing with endogenous ligands or substrates at structurally-defined binding sites on receptors.

Antagonists display no efficacy to activate the receptors they bind. Once bound, however, antagonists may inhibit the function of agonists, inverse agonists and partial agonists. In functional antagonist assays, a dose-response curve measures the effect of the ability of a range of concentrations of antagonists to reverse the activity of an agonist. The potency of an antagonist is usually defined by its $IC_{50}$ value. This can be calculated for a given antagonist by determining the concentration of antagonist needed to elicit half inhibition of the maximum biological response of an agonist. The lower the $IC_{50}$, the greater the potency of the antagonist.

Competitive, or orthosteric, antagonists reversibly bind to receptors at the same binding site (active site) as the ligand or agonist, but without activating the receptor, thereby competing with agonist for the same binding site on the receptor. Non-competitive, or allosteric, antagonists bind to a separate binding site from the agonist, exerting their action to that receptor via that separate binding site. Thus, they do not compete with agonists for binding. Uncompetitive antagonists differ from non-competitive antagonists in that they require receptor activation by an agonist before they can bind to a separate allosteric binding site.

"Insulin resistance" describes a condition in which physiological amounts of insulin are inadequate to produce a normal insulin response from cells or tissues.

The present disclosure encompasses use of insulin-INSR signaling complex modulators that offer unique advantages over existing therapies. They act at the level of the INSR, which should allow induction of the entire range of actions of insulin while minimizing unwanted side effects. It is hypothesized that the antibodies can provide more precise control of glucose and insulin levels. Targeting the extracellular region of the INSR allows for the use of biological molecules as insulin-INSR signaling complex modulators that modulate the effect of endogenous insulin; these may have advantages such as improved half-life, reduced dosage or frequency of dosage, reduced toxicity and greater ease of manufacture.

Methods of identifying antibodies that are modulators of insulin signaling are disclosed in co-owned U.S. Pat. No. 8,926,976 and patent application U.S. Ser. No. 14/555,233 and U.S. Ser. No. 12/890,590, herein incorporated by reference.

The Insulin Receptor (INSR)

The INSR is a tyrosine kinase receptor found in organisms as primitive as cnidarians and insects. In higher organisms it is essential for glucose homeostasis. Mouse knockout studies have also shown the INSR to be important in adipogenesis, neovascularization, the regulation of hepatic glucose synthesis and glucose-induced pancreatic insulin secretion (Kitamura et al, Ann. Rev. Physiol., 65: 313-332 2003). INSR signaling is also important in the brain, where it is involved in the regulation of food intake, peripheral fat deposition and the reproductive endocrine axis as well as in learning and memory (Wada et al, J. Pharmacol. Sci. 99: 128-143, 2005). Dysfunctional INSR signaling has been implicated in diseases including type I and type II diabetes, dementia and cancer.

The domains of the closely related insulin-like growth factor receptor (IGFR-1) exhibit high (47-67%) amino acid identity with the INSR. While similar in structure, IGF-IR and INSR serve different physiological functions. IGF-IR is expressed in almost all normal adult tissue except for liver, which is itself the major site of IGF-I production. INSR is primarily involved in metabolic functions whereas IGF-IR mediates growth and differentiation (Adams et al, Cell. Mol. Life Sci. 57: 1050-1093, 2000).

INSR exists as two splice variant isoforms, INSR-A and INSR-B, which respectively lack or contain the 12 amino acids coded by exon 11. The longer variant, INSR-B, is the isoform responsible for signaling metabolic responses. In contrast, INSR-A signals predominantly mitogenic responses, is the preferentially expressed isoform in several cancers (Denley et al., Horm. Metab. Res. 35: 778-785, 2003) and is capable of binding insulin-like growth factor 2 (IGF-II) with high affinity (Denley et al, Mol. Endocrinol. 18: 2502-2512, 2004).

The mature human INSR is a homodimer comprising two α subunits and two β subunits (chains). The α and β chains are encoded by a single gene and arise from the post-translational cleavage of a 1370 amino acid precursor at a furin cleavage site located at residues 720-723. The α-chain and 194 residues of the β-chain comprise the extracellular protion of the INSR. There is a single transmembrane sequence and a 403 residue cytoplasmic domain containing a tyrosine kinase. The N-terminal half of each ectodomain monomer consists of two homologous leucine-rich repeat domains (L1 and L2) of approximately 150 amino acids, separated by a cysteine-rich region (CR), also approximately 150 amino acids in size. The C-terminal half of each ectodomain monomer (approximately 460 residues) consists of three fibronectin type III domains (FnIII-1, FnIII-2 and FnIII-3). The FnIII-2 domain contains an insert domain (ID) of approximately 120 residues, within which lies the furin cleavage site that generates the α and β chains of the mature receptor. Intracellularly, each monomer contains a tyrosine kinase catalytic domain flanked by two regulatory regions (the juxtmembrane region and the C-tail) that contain the phosphotyrosine binding sites for signaling molecules (Ward et al, Acta Physiol. 192: 3-9, 2008).

Models for insulin binding proposes that, in the basal state, the INSR homodimer contains two identical pairs of binding sites (referred to as Site 1 and Site 2) on each monomer (De Meyts, Bioessays, 26: 1351-1362, 2004). Binding of insulin to a low affinity site (Site 1) on one α-subunit is followed by a second binding event between the bound insulin and a different region of the second INSR α-subunit (Site 2). This ligand-mediated bridging between the two α subunits generates the high affinity state that results in signal transduction. In contrast, soluble INSR ectodomain, which is not tethered at its C-terminus, cannot generate the high affinity receptor-ligand complex. It can bind two molecules of insulin simultaneously at its two Site 1's, but only with low affinity (Adams et al, Cell. Mol. Life Sci. 57: 1050-1093, 2000). Site 1 is thought to be comprised of elements from the central β-sheet of the L1 domain and the last 16 residues of the α-chain (referred to as the CT peptide). Site 2 most likely includes the loops at the junction of FnIII-1 and FnIII-2. Insulin binding is thought to involve structural changes in both insulin and its receptor (Ward and Lawrence, BioEssays 31: 422-434, 2009).

Once an insulin molecule has docked onto the receptor and effected its action, it may be released back into the extracellular environment or it may be degraded by the cell. Degradation normally involves endocytosis of the insulin-INSR complex followed by the action of insulin degrading enzyme. Most insulin molecules are degraded by liver cells. It has been estimated that a typical insulin molecule is finally degraded about 71 minutes after its initial release into circulation (Duckworth et al, Endocr. Rev. 19(5): 608-24, 1998).

Insulin Signaling

Insulin induces a signaling network of molecules, carrying the information from the INSR to the effector proteins involved in metabolism and growth. Insulin binding to INSR induces a conformational change that promotes activation of an intrinsic tyrosine kinase activity, leading to autophosphorylation of the INSR β-subunit. Insulin receptor substrate (IRS) proteins are recruited to the plasma membrane through an interaction with the phosphorylated INSR, and these also become phosphorylated on tyrosine residues, promoting recruitment of additional signaling proteins to the complex resulting in signaling through two major pathways (1) the PI3 kinase/PDK1/PKB pathway which primarily regulates metabolism, with some influence on growth, and (2) the Ras/ERK mitogenic pathway which primarily regulates cell growth.

Certain marketed insulin analogues have been reported to display IGF-1-like mitogenic and anti-apoptotic activities in cultured cancer cells, raising questions over their long-term safety in humans (Weinstein et al, Diabetes Metab Res Rev 25: 41-49, 2009).

Types and Sources of Antibodies

The present disclosure encompasses use of target specific antibodies that bind to insulin receptor or the insulin/insulin receptor complex. In exemplary embodiments, a target specific antibody described herein can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

The term "antibody" is used in the broadest sense and includes fully assembled antibodies, tetrameric antibodies, monoclonal antibodies, polyclonal antibodies, multispecific antibodies (e.g., bispecific antibodies), human and humanized antibodies, antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, as long as the antibody retains the desired biological activity.

In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk, (*J. Mol. Biol.* 196:901-917, 1987); Chothia et al., (*Nature* 342:878-883, 1989).

The hypervariable region of an antibody refers to the CDR amino acid residues of an antibody which are responsible for antigen-binding. The hypervariable region comprises amino acid residues from a CDR [i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196: 901-917 (1987)]. However, one of skill in the art understands that the actual location of the CDR residues may vary from the projected residues described above when the sequence of the particular antibody is identified.

Framework or FR residues are those variable domain residues other than the hypervariable region residues.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody used herein, if it comprises a constant domain, may be of any of these subclasses or isotypes.

In exemplary embodiments, an antibody used in the methods can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, monoclonal antibodies are advantageous in that they are synthesized by the homogeneous culture, uncontaminated by other immunoglobulins with different specificities and characteristics.

Monoclonal antibodies to be used in accordance with the present disclosure may be made by the hybridoma method first described by Kohler et al., (*Nature*, 256:495-7, 1975), or may be made by recombinant DNA methods (see, e.g., U.S. Pat. No. 4,816,567). The monoclonal antibodies may also be isolated from phage antibody libraries using the techniques described in, for example, Clackson et al., (*Nature* 352:624-628, 1991) and Marks et al., (*J. Mol. Biol.* 222:581-597, 1991).

In the hybridoma method, a mouse or other appropriate host animal, such as a hamster or macaque monkey, is immunized to elicit lymphocytes that produce or are capable of producing antibodies that will specifically bind to the protein used for immunization (Harlow & Lane; Antibodies: A Laboratory Manual, Cold Spring Harbor Laboratory Press: Cold Spring Harbor, N.Y. (1988).

Recombinant Production of Antibodies

The present disclosure also encompasses nucleic acid molecules encoding antibodies useful in the present methods. In some embodiments, different nucleic acid molecules encode a heavy chain variable region and a light chain variable region of an antigen-specific antibody. In other embodiments, the same nucleic acid molecule encodes a heavy chain and a light chain variable regions of an antigen-specific antibody.

DNA encoding a monoclonal antibody described herein may be isolated and sequenced from a hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, (*Proc. Natl. Acad. Sci. USA,* 87:6450-54 (1990)), each of which is incorporated herein by reference. In one embodiment, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard phage display techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The disclosure also provides isolated nucleic acid encoding antibodies contemplated herein, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Various systems and methods for antibody production are reviewed by Birch & Racher (Adv. Drug Deliv. Rev. 671-685 (2006)).

For recombinant production of the antibody, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia* pastors (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, petunia, tomato, tobacco, lemna, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol*. 36: 59, 1977); baby hamster kidney cells (BHK, ATCC CCL 10); mouse sertoli cells (TM4, Mather, (*Biol. Reprod*. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci*. 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired antibody nucleic acid sequences may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., (*Meth. Enz.* 58: 44, 1979), Barnes et al., *Anal. Biochem.* 102: 255 (1980), U.S. Pat. Nos. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al. (*Science* 240:1041-43, 1988; ICSU Short Reports 10:105 (1990); and *Proc. Natl. Acad. Sci. USA* 90:457-461 (1993) describe a procedure for isolating antibodies which are secreted to the periplasmic space of *E. coli*. [See also, (Carter et al., *Bio/Technology* 10:163-167 (1992)].

The antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13, 1983). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Figure 6:
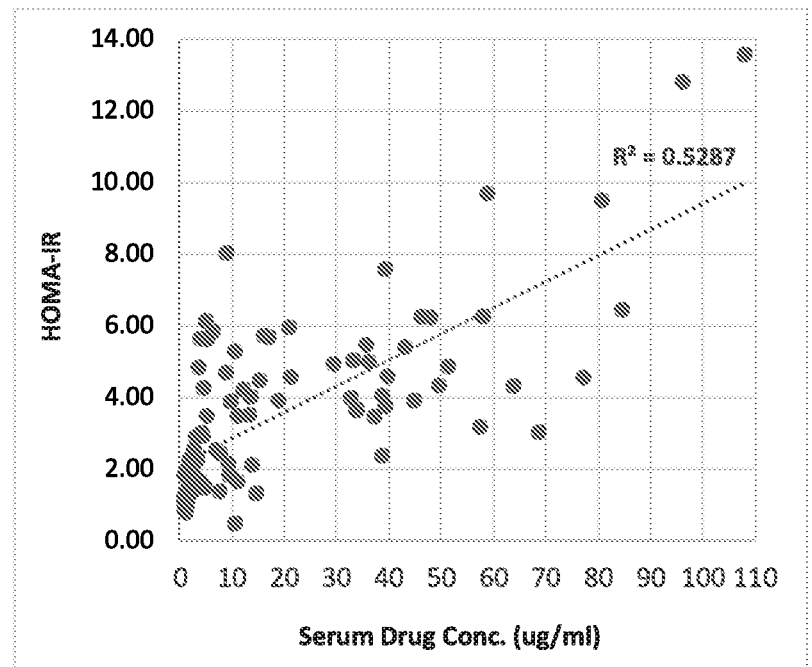
FIG. 6 shows Serum Drug Concentration Versus HOMA-IR for Ab081-Treated Subjects Across Days 1-7.

Amino acid sequences of exemplary antibodies are set out in FIG. 6.

In exemplary embodiments, the method contemplates use of:

a monoclonal antibody that retains any one, two, three, four, five, or six of HCDR1, HCDR2, HCDR3, LCDR1, LCDR2, or LCDR3 of any one of SEQ ID NOs: 11-25 and SEQ ID NOs: 26-40, respectively, optionally including one or two mutations in any of such CDR(s), e.g., a conservative or non-conservative substitution;

a monoclonal antibody that retains all of HCDR1, HCDR2, HCDR3, or the heavy chain variable region of any one of SEQ ID NOs: 11-25, optionally including one or two mutations in any of such CDR(s), optionally further comprising any suitable heavy chain constant region, e.g., IgG1, IgG2, IgG3, IgG4, IgM, IgA1, IgA2, or IgE, a human sequence thereof, or a hybrid thereof or a human consensus thereof;

a monoclonal antibody that retains all of LCDR1, LCDR2, LCDR3, or the light chain variable region of any one SEQ ID NOs: 26-40, optionally including one or two mutations in any of such CDR(s), optionally further comprising to any suitable light chain constant region, e.g. a kappa or lambda light chain constant region, a human sequence thereof, or a hybrid thereof or a human consensus thereof;

a monoclonal antibody that binds to the same linear or three-dimensional epitope of INSR as an antibody comprising variable regions set out in SEQ ID NO: 1-10, e.g., as determined through X-ray crystallography or other biophysical or biochemical techniques such as deuterium exchange mass spectrometry, alanine scanning and peptide fragment ELISA;

a monoclonal antibody that competes with an antibody comprising variable regions set out in SEQ ID NO: 1-10 for binding to human INSR by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, all three heavy chain CDRs, or all six CDRs of the light and heavy chain, paired as set forth in Table 1. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g. heavy or light) of any of antibodies, e.g. to form a suitable heavy or light chain variable region.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NO: 1-5 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NO: 6-10, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs set out in SEQ ID NO: 26-40. In other embodiments, the amino acid sequence with percentage identity to the heavy chain variable region may comprise one, two, or three of the heavy chain CDRs set out in SEQ ID NO: 11-25.

It is contemplated that the antibodies used herein may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

It is further contemplated that the disclosure provides use of a purified polypeptide comprising any one of the amino acid sequences of SEQ ID NO: 1-5 fused to any one of the amino acid sequences of SEQ ID NO: 6-10, or fragments thereof that include at least a portion of SEQ ID NO: 1-5 and SEQ ID NO: 6-10, wherein the polypeptide binds insulin receptor or the insulin/insulin receptor complex.

In another aspect, the disclosure provides for use of a purified polypeptide comprising at least one CDR of a light chain variable region described herein, wherein the light chain variable region comprises an amino acid sequence at least 90% identical to the LCDR sequences set out in SEQ ID NO: 26-40. In one embodiment, the polypeptide may be 90%, 95%, 96%, 97%, 98%, or 99% identical to any one of the LCDRs set out in SEQ ID NO: 26-40. In a further aspect, the disclosure contemplates use of a purified polypeptide comprising at least one CDR of a heavy chain variable region described herein, wherein the heavy chain variable region comprises an amino acid sequence at least 90% identical to the HCDR sequences set out in SEQ ID NO: 11-25. In one embodiment, the polypeptide may be 90%, 95%, 96%, 97%, 98%, or 99% identical to any one of the HCDRs set out in SEQ ID NO: 11-25.

It is further contemplated that the CDR of the antibody heavy and light chains comprise variant amino acid sequences which may improve antibody binding affinity and are derived through, for example, affinity maturation. In one aspect it is contemplated that an antibody used herein comprises a heavy chain HCDR2 sequence having about 35% identity to a HCDR2 of a parent antibody sequence set out in SEQ ID NOs: 12, 15, 18, 21 and 24. In a related aspect it is contemplated that an antibody used herein comprises a heavy chain HCDR3 sequence having about 50% identity to a HCDR3 of a parent antibody sequence set out in SEQ ID NOs: 13, 16, 19, 22 and 25.

In one embodiment the disclosure contemplates use of antigen-binding compounds, including functional fragments, having a variable region amino acid sequence set forth in any one of SEQ ID NOs: 1-5 and 6-10. In a related embodiment, an aforementioned antigen binding compound is selected from the group consisting of a fully assembled tetrameric antibody, a polyclonal antibody, a monoclonal antibody including a HUMAN ENGINEERED™ antibody; a humanized antibody; a human antibody; a chimeric antibody; a multispecific antibody, an antibody fragment, Fab, F(ab')$_2$; Fv; scFv or single-chain antibody fragment; a diabody; triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a $V_{HH}$ containing antibody, or a variant or derivative of any one of these antibodies, that comprise one or more CDR sequences of the antibody and exhibit the desired biological activity. The antigen binding compounds preferably retain binding affinity of $10^{-5}$, $10^{-6}$, $10^{-7}$, $10^{-8}$, $10^{-9}$, $10^{-10}$, $10^{-11}$ M or less as measured by surface plasmon resonance.

In one aspect, the antibodies useful in the present methods comprise a heavy chain variable region or light chain variable region as set out in amino acid sequences SEQ ID NO: 1-5 and SEQ ID NO: 6-10, respectively, optionally as paired in Table 1.

TABLE 1

| Antibody | Heavy Chain Variable SEQ ID NO: | HCDR1, HCDR2, HCDR3 SEQ ID NO: | Light Chain Variable SEQ ID NO: | LCDR1, LCDR2, LCDR3 SEQ ID NO: |
|---|---|---|---|---|
| Ab081 | 1 | 11-13 | 6 | 26-28 |
| Ab061 | 2 | 14-16 | 7 | 29-31 |
| Ab070 | 3 | 17-19 | 8 | 32-34 |
| Ab020 | 4 | 20-22 | 9 | 35-37 |
| Ab052 | 5 | 23-25 | 10 | 38-40 |

It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 11-25, or at least one of CDR1, CDR2 or CDR3 of the light chain of SEQ ID NOs: 26-40, as paired in Table 1.

In one embodiment, the heavy chain comprises an amino acid sequence identified as a heavy chain CDR3 sequence. Such a "heavy chain CDR3 sequence" (HCDR3) includes an amino acid sequence identified as a heavy chain CDR3 sequence set out in SEQ ID NOs: 13, 16, 19, 22, and 25. Alternatively, the HCDR3 sequence comprises an amino acid sequence that contains one or more amino acid changes compared to any HCDR3 amino acid sequence set out in SEQ ID NOs: 13, 16, 19, 22 and 25, i.e., a substitution, insertion or deletion. Preferable substitutions include a substitution to an amino acid at the corresponding position within another HCDR3 herein. Alternatively, the HCDR3 sequence may comprise a consensus amino acid sequence of the HCDR3 described herein.

The heavy chain comprising a HCDR3 sequence of the antibody described above may further comprise a "heavy chain CDR1 sequence", which includes any of the amino acid sequences identified as a heavy chain CDR1 in SEQ ID NO: 11, 14, 17, 20 and 22, amino acid sequences that contain one or more amino acid changes compared to any heavy chain CDR1 identified in SEQ ID NO: 11, 14, 17, 20 and 22, preferably a substitution to an amino acid at the corresponding position within another heavy chain CDR1 herein, or a consensus sequence of heavy chain CDR1 described herein.

Alternatively, the heavy chain comprising a HCDR3 sequence of the antibody described above may further comprise a "heavy chain CDR2 sequence" (HCDR2), which includes any of the amino acid sequences identified as an HCDR2 in SEQ ID NO: 12, 15, 18, 21 and 24, amino acid sequences that contain one or more amino acid changes compared to any HCDR2 identified in SEQ ID NO: 12, 15, 18, 21 and 24, or a consensus sequence of heavy chain CDR2 described herein.

The heavy chain comprising a heavy chain CDR3 sequence described above may also comprise both (a) a heavy chain CDR1 sequence described above and (b) a heavy chain CDR2 sequence described above.

One aspect of the disclosure contemplates use of an antibody that binds target antigen comprising a heavy chain that comprises any one, two, and/or three of the heavy chain CDR sequences described herein.

Any of the heavy chain CDR sequences described above may also include amino acids added to either end of the CDRs. Preparation of variants and derivatives of antibodies and antigen-binding compounds, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a human antibody sequence.

Antibodies comprising any one of the heavy chains described above may further comprise a light chain, preferably a light chain that binds to target antigen, and most preferably a light chain comprising light chain CDR sequences described below.

Another aspect of the disclosure provides use of an antibody that binds target antigen comprising a light chain that comprises any one, two, and/or three of the light chain CDR sequences described below.

Preferably the light chain comprises an amino acid sequence identified as a light chain CDR3 sequence. Such a "light chain CDR3 sequence" (LCDR3) includes an amino acid sequence identified as a light chain CDR3 sequence set out in SEQ ID NOs: 28, 31, 34, 37 and 40. Alternatively, the light chain CDR3 sequence comprises an amino acid sequence that contains one or more amino acid changes compared to any light chain CDR3 amino acid sequence set out in SEQ ID NOs: 28, 31, 34, 37 and 40, i.e. a substitution, insertion or deletion or a consensus sequence of light chain CDR3 described herein.

The light chain comprising a light chain CDR3 sequence described above may further comprise a "light chain CDR1 sequence", which includes any of the amino acid sequences identified as a light chain CDR1 in SEQ ID NO: 26, 29, 32, 35 and 38, amino acid sequences that contain one or more amino acid changes compared to any light chain CDR1 identified in SEQ ID NO: 26, 29, 32, 35 and 38, preferably a substitution to an amino acid at the corresponding position within another light chain CDR1 herein, or a consensus sequence of light chain CDR1 described herein.

Alternatively, the light chain comprising a light chain CDR3 sequence described above may further comprise a "light chain CDR2 sequence", which includes any of the amino acid sequences identified as a light chain CDR2 in SEQ ID NO: 27, 30, 33, 36 and 39, amino acid sequences that contain one or more amino acid changes compared to any light chain CDR2 of SEQ ID NO: 27, 30, 33, 36 and 39, preferably a substitution to an amino acid at the corresponding position within another light chain CDR2 of SEQ ID NO: 27, 30, 33, 36 and 39, or a consensus sequence of light chain CDR2.

In a related aspect, the disclosure contemplates use of a purified polypeptide comprising at least one HCDR of SEQ ID NO: 11-25 or LCDR of SEQ ID NO: 26-40, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a human antibody sequence. For example, within each heavy chain framework region (H-FR1-4) it is contemplated that at least one, at least two, at least three, at least four, at least five, or at least six native framework region residues of the murine heavy chain variable region have been altered by amino acid substitution, and wherein within each light chain framework region (L-FR1-4), at least one, at least two, at least three, at least four, at least five or at least six native framework residues of the murine light chain variable region have been altered by amino acid substitution.

The light chain comprising a light chain CDR3 sequence described above may also comprise both (a) a light chain CDR1 sequence described above and (b) a light chain CDR2 sequence described above.

Antibodies comprising any one of the light chain variable regions described above may further comprise a heavy chain variable region, optionally paired as described in Table 1, preferably a heavy chain variable region that binds to target antigen, and most preferably a heavy chain variable region comprising heavy chain CDR sequences described above.

In a related embodiment, the negative modulator antibody includes, but is not limited to the following antibodies: Ab081 (SEQ ID NO: 1 and 6), Ab061 (SEQ ID NO: 2 and 7), Ab070 (SEQ ID NO: 3 and 8), Ab020 (SEQ ID NO: 4 and 9), and Ab052 (SEQ ID NO: 5 and 10).

In a further aspect, the antibody is an antibody that competes with any of the antibodies described herein for binding to the insulin receptor or insulin/insulin receptor complex. In certain embodiments, the antibody exhibits partial competition. In a related embodiment, partial competition is competition of about 30% to 70%, about 30% to 80%, or about 30%, 35%, 40%, 45%, 50%, 55%, 60%, 65%, 70%, 75%, or 80%. In some embodiments, the antibody exhibits complete competition. In one embodiment, complete competition is competition of greater than 70%, 75%, 80%, 85%, 90%, 95% or 100%. Exemplary assays for measuring antibody competition include, but are not limited to, receptor loading assays and epitope binning assays as described in the art.

Antibody Fragments

Antibody fragments comprise a portion of an intact full length antibody, preferably an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; V$_{HH}$ containing antibodies; and other polypeptides formed from antibody fragments. See for example Holliger & Hudson (Nat. Biotech. 23(9) 1126-36 (2005)).

Papain digestion of antibodies produces two identical antigen-binding fragments, called "Fab" fragments, monovalent fragments consisting of the V$_L$, V$_H$, C$_L$ and C$_H$ domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the V$_H$ and V$_L$ domains of antibody, wherein these domains are present in a single polypeptide chain. Preferably, the Fv polypeptide further comprises a polypeptide linker between the $V_H$ and $V_L$ domains that enables the Fv to form the desired structure for antigen binding, resulting in a single-chain antibody (scFv), in which a $V_L$ and $V_H$ region are paired to form a monovalent molecule via a synthetic linker that enables them to be made as a single protein chain (Bird et al., *Science* 242:423-426, 1988, and Huston et al., *Proc. Natl. Acad. Sci. USA* 85:5879-5883, 1988). For a review of scFv see Pluckthun, in The Pharmacology of Monoclonal Antibodies, vol. 1 13, Rosenburg and Moore eds., Springer-Verlag, New York, pp. 269-315 (1994). An Fd fragment consists of the $V_H$ and $C_H1$ domains.

Additional antibody fragments include a domain antibody (dAb) fragment (Ward et al., *Nature* 341:544-546, 1989) which consists of a $V_H$ domain. Diabodies are bivalent antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks (Nuttall et al., *Mol Immunol.* 38:313-26, 2001) and Camelidae (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure $H_2L_2$ (referred to as "heavy-chain antibodies" or "HCAbs"). Camelid $V_{HH}$ reportedly recombines with IgG2 and IgG3 constant regions that contain hinge, CH2, and CH3 domains and lack a CH1 domain (Hamers-Casterman et al., supra). For example, llama IgG1 is a conventional ($H_2L_2$) antibody isotype in which $V_H$ recombines with a constant region that contains hinge, CH1, CH2 and CH3 domains, whereas the llama IgG2 and IgG3 are heavy chain-only isotypes that lack CH1 domains and that contain no light chains. Camelid $V_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Classical $V_H$-only fragments are difficult to produce in soluble form, but improvements in solubility and specific binding can be obtained when framework residues are altered to be more $VH_H$-like. (See, e.g., Reichman, et al., J Immunol Methods 1999, 231:25-38.) Methods for generating antibodies having camelid heavy chains are described in, for example, in U.S. Patent Publication Nos. 20050136049 and 20050037421.

The variable domain of an antibody heavy-chain is has a molecular mass of 15 kDa, and is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Revets et al, Expert Opin. Biol. Ther. 5(1): 111-24 (2005).

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab.

A "minibody" consisting of scFv fused to CH3 via a peptide linker (hingeless) or via an IgG hinge has been described in Olafsen, et al., Protein Eng Des Sel. 2004 April; 17(4):315-23.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al (*EMBO J* 14:1542-51, 1995) and Wheeler et al. (*FASEB J.* 17:1733-5. 2003). Transbodies are cell-permeable antibodies in which a protein transduction domain (PTD) is fused with single chain variable fragment (scFv) antibodies Heng et al., (*Med Hypotheses.* 64:1105-8, 2005).

Further contemplated are antibodies that are SMIPs or binding domain immunoglobulin fusion proteins specific for an antigen. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

In yet another embodiment, the antibody or antigen-binding compound comprises a constant region and one or more heavy and light chain variable framework regions of a human antibody sequence. In a related embodiment, the antibody comprises a modified or unmodified constant region of a human IgG1, IgG2, IgG3 or IgG4.

Alternatively, antibody fragments may be fused to a protein scaffold. Libraries of protein scaffolds include, but are not limited to, Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1 β-lactamase, fibronectin type III domains, CTLA-4, T-cell resptors, knottins, neocarzinostatin, carbohydrate binding module 4-2, green fluorescent protein, thioredoxin (Gebauer & Skerra, Curr. Opin. Chem. Biol. 13:245-55 (2009); Gill & Damle, Curr. Opin. Biotech 17: 653-58 (2006); Hosse et al, Protein Sci. 15:14-27 (2006); Skerra, Curr. Opin. Biotech 18: 295-3-4 (2007)).

Thus, a variety of compositions comprising one, two, and/or three CDRs of a heavy chain variable region or a light chain variable region of an antibody may be generated by techniques known in the art.

Chimeric And Humanized Antibodies

Because chimeric or humanized antibodies are less immunogenic in humans than the parental mouse monoclonal antibodies, they can be used for the treatment of humans with far less risk of anaphylaxis.

Chimeric monoclonal antibodies, in which the variable Ig domains of a mouse monoclonal antibody are fused to human constant Ig domains, can be generated using standard procedures known in the art (See Morrison et al., *Proc. Natl. Acad. Sci. USA* 81, 6841-6855 (1984); and, Boulianne et al, *Nature* 312, 643-646, (1984)). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting") (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely affect either antigen binding or protein folding, but likely to reduce immunogenicity in a human environment (a process referred to in the art as HUMAN ENGINEERING™). In the present disclosure, humanized antibodies will include both "humanized", "veneered" and "HUMAN ENGINEERED™" antibodies. These methods are disclosed in, e.g., Jones et al., *Nature* 321:522 525 (1986); Morrison et al., *Proc. Natl. Acad. Sci., U.S.A.,* 81:6851-6855 (1984); Morrison and Oi, *Adv. Immunol.,* 44:65-92 (1988); Verhoeyer et al., *Science* 239:1534-1536 (1988); Padlan, *Molec. Immun.* 28:489-498 (1991); Padlan, *Molec. Immunol.* 31:169-217 (1994); Kettleborough et al., *Protein Eng.* 4:773-783 (1991); Studnicka et al. U.S. Pat. No. 5,766,886; Studnicka et al., (*Protein Eng* 7: 805-814, 1994) each of which is incorporated herein by reference.

Human Antibodies from Transgenic Animals

Human antibodies to antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598 6,657,103 and 6,833,268.

Using a transgenic animal described above, an immune response can be produced to a selected antigen, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigens including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. patent application no. 20030194404; and U.S. patent application no. 20030031667.

Additional transgenic animals useful to make monoclonal antibodies include the Medarex HuMAb-MOUSE®, described in U.S. Pat. No. 5,770,429 and Fishwild, et al. (*Nat. Biotechnol.* 14:845-851 (1996)), which contains gene sequences from unrearranged human antibody genes that code for the heavy and light chains of human antibodies. Immunization of a HuMAb-MOUSE® enables the production of fully human monoclonal antibodies to the antigen.

Also, Ishida et al. (*Cloning Stem Cells.* 4:91-102 (2002)) describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., *Proc. Natl. Acad. Sci. USA,* 90:2551 (1993); Jakobovits et al., *Nature,* 362:255-258 (1993); Bruggermann et al., *Year in Immunol.,* 7:33 (1993); and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

The disclosure contemplates a method for producing antigen-specific antibody or antigen-binding portion thereof comprising the steps of synthesizing a library of human antibodies on phage, screening the library with antigen or a portion thereof, isolating phage that bind antigen, and obtaining the antibody from the phage. By way of example, one method for preparing the library of antibodies for use in phage display techniques comprises the steps of immunizing a non-human animal comprising human immunoglobulin loci with antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant antigen-specific antibodies useful herein may be obtained in this way. In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies can be isolated by screening of a recombinant combinatorial antibody library, preferably a scFv phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum. Antibod. Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J. Mol. Biol. 226:889-896; Clackson et al. (1991) Nature 352:624-628; Gram et al. (1992) Proc. Natl. Acad. Sci. USA 89:3576-3580; Garrad et al. (1991) Bio/Technology 9:1373-1377; Hoogenboom et al. (1991) Nuc Acid Res 19:4133-4137; and Barbas et al. (1991) Proc. Natl. Acad. Sci. USA 88:7978-7982.

In one embodiment, to isolate human antibodies specific for an antigen, with the desired binding characteristics, a human $V_H$ and $V_L$ library are screened to select for antibody fragments having the desired specificity. The antibody libraries used in this method are preferably scFv libraries prepared and screened as described herein and in the art (McCafferty et al., PCT Publication No. WO 92/01047, McCafferty et al., (Nature 348:552-554 (1990)); and Griffiths et al., (EMBO J 12:725-734 (1993)). The scFv antibody libraries preferably are screened using the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., J. Mol. Biol., 227:381 (1991); Marks et al., J. Mol. Biol, 222:581-597 (1991); U.S. Pat. Nos. 5,565,332 and 5,573,905; Clackson, T., and Wells, J. A., TIBTECH 12, 173-184 (1994)). In particular, in vitro selection and evolution of antibodies derived from phage display libraries has become a powerful tool (See Burton, D. R., and Barbas III, C. F., Adv. Immunol. 57, 191-280 (1994); Winter, G., et al., Annu. Rev. Immunol. 12, 433-455 (1994); U.S. patent publication no. 20020004215 and WO 92/01047; U.S. patent publication no. 20030190317; and U.S. Pat. Nos. 6,054,287 and 5,877,293.

Watkins, "Screening of Phage-Expressed Antibody Libraries by Capture Lift," Methods in Molecular Biology, Antibody Phage Display: Methods and Protocols 178:187-193 (2002), and U.S. patent publication no. 20030044772, published Mar. 6, 2003, describe methods for screening phage-expressed antibody libraries or other binding molecules by capture lift, a method involving immobilization of the candidate binding molecules on a solid support.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, fl, Ifl, Ike, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairs of the initially selected $V_L$ and $V_H$ segments are screened for antigen binding, may be performed to select preferred $V_L/V_H$ pair combinations. Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to antigen.

Following screening and isolation of an antigen-specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3, hyperphage; and phage displaying or encoding a binding molecule fused to a capsid protein.

Antibodies may also be generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, (*Bio/Technology*, 10:779-783 (1992)).

Methods for display of polypeptides on the surface of viruses, yeast, microbial and mammalian cells have also been used to identify antigen specific antibodies. See, for example, U.S. Pat. Nos. 5,348,867; 5,723,287; 6,699,658; Wittrup, Curr Op. Biotech. 12:395-99 (2001); Lee et al, Trends in Biotech. 21(1) 45-52 (2003); Surgeeva et al, Adv. Drug Deliv. Rev. 58: 1622-54 (2006). Antibody libraries may be attached to yeast proteins, such as agglutinin, effectively mimicking the cell surface display of antibodies by B cells in the immune system.

In addition to phage display methods, antibodies may be isolated using in vitro display methods including ribosome display and mRNA display (Amstutz et al, Curr. Op. Biotech. 12: 400-05 (2001)). Selection of polypeptide using ribosome display is described in Hanes et al., (*Proc. Natl Acad Sci USA*, 94:4937-4942 (1997)) and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, Curr. Opin. Immunol. 20: 471-78 (2008).

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., *Biotechnol Bioeng.* 87:614-22 (2004)). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., *Mol Immunol.* 26:1113-23 (1989)). Some host cell strains, e.g. Lec13 or rat hybridoma YB2/0 cell line naturally produce antibodies with lower fucosylation levels. (Shields et al., *J Biol Chem.* 277:26733-40 (2002); Shinkawa et al., *J Biol Chem.* 278: 3466-73 (2003)). An increase in the level of bisected carbohydrate, e.g. through recombinantly producing antibody in cells that overexpress GnTIII enzyme, has also been determined to increase ADCC activity (Umana et al., *Nat Biotechnol.* 17:176-80 (1999)). It has been predicted that the absence of only one of the two fucose residues may be sufficient to increase ADCC activity (Ferrara et al., *Biotechnol Bioeng.* 93:851-61 (2006)).

Variants with Altered Effector Function

Other modifications of the antibody are contemplated. In one aspect, it may be desirable to modify the antibody useful in the methods with respect to effector function, for example, to enhance the effectiveness of the antibody in treating cancer (Natsume et al, Drug Design Dev't & Ther. 3: 7-16 (2009). Exemplary effector functions include C1q binding; CDC; Fc receptor binding; ADCC; phagocytosis; down regulation of cell surface receptors (e.g. B cell receptor; BCR), etc. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., (*J. Exp Med.* 176: 1191-1195 (1992)) and Shopes, B. (*J.*

*Immunol.* 148: 2918-2922 (1992)). Homodimeric antibodies with enhanced anti-tumor activity may also be prepared using heterobifunctional cross-linkers as described in Wolff et al., (*Cancer Research* 53: 2560-2565 (1993)). Alternatively, an antibody can be engineered which has dual Fc regions and may thereby have enhanced complement lysis and ADCC capabilities. See Stevenson et al., (*Anti-Cancer Drug Design* 3: 219-230 (1989)). In addition, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Also see Steplewski et al., (*Proc Natl Acad Sci USA*. 85:4852-56 (1998)), which described chimeric antibodies wherein a murine variable region was joined with human gamma 1, gamma 2, gamma 3, and gamma 4 constant regions.

In certain embodiments of the disclosure, it may be desirable to use an antibody fragment, rather than an intact antibody, to increase tumor penetration, for example. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

The salvage receptor binding epitope preferably constitutes a region wherein any one or more amino acid residues from one or two loops of an Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or VH region, or more than one such region, of the antibody. Alternatively, the epitope is taken from the CH2 domain of the Fc region and transferred to the $C_L$ region or $V_L$ region, or both, of the antibody fragment. See also International applications WO 97/34631 and WO 96/32478 which describe Fc variants and their interaction with the salvage receptor.

Thus, antibodies contemplated herein may comprise a human Fc portion, a human consensus Fc portion, or a variant thereof that retains the ability to interact with the Fc salvage receptor, including variants in which cysteines involved in disulfide bonding are modified or removed, and/or in which the a met is added at the N-terminus and/or one or more of the N-terminal 20 amino acids are removed, and/or regions that interact with complement, such as the C1q binding site, are removed, and/or the ADCC site is removed [see, e.g., Sarmay et al., *Molec. Immunol.* 29:633-9 (1992)].

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., (*J. Biol. Chem.*, 276:6591-604 (2001)), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., (*Biochem. Soc. Trans.* 30:487-490, 2001), incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity.

Covalent Modifications

Covalent modifications of the polypeptide binding agents, e.g., antibodies, are also included within the scope of this disclosure. They may be made by chemical synthesis or by enzymatic or chemical cleavage of the polypeptide binding agent, if applicable. Other types of covalent modifications of the polypeptide binding agent are introduced into the molecule by reacting targeted amino acid residues of the polypeptide binding agent with an organic derivatizing agent that is capable of reacting with selected side chains or the N- or C-terminal residues.

Other modifications include histidlyl, lysinyl arginyl, tyrosyl, glutaminyl and asparaginyl hydroxylation of proline and lysine. Methods for making such modifications are disclosed in U.S. Pat. No. 8,926,976, incorporated herein by reference, and in the art.

Derivatives

Derivative refers to polypeptide binding agents, including antibodies, chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the polypeptide binding agents described herein, such as an antibody, are also useful as therapeutic agents and may be produced by methods described herein The conjugated moiety can be incorporated in or attached to a polypeptide binding agent either covalently, or through ionic, van der Waals or hydrogen bonds, e.g., incorporation of radioactive nucleotides, or biotinylated nucleotides that are recognized by streptavadin.

Polyethylene glycol (PEG) may be attached to the polypeptide binding agents to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the polypeptide binding agents via acylation or reductive alkylation through a natural or engineered reactive group on the PEG moiety (e.g., an aldehyde, amino, thiol, or ester group) to a reactive group on the polypeptide binding agent (e.g., an aldehyde, amino, or ester group). Addition of PEG moieties to polypeptide binding agents can be carried out using techniques well-known in the art. See, e.g., International Publication No. WO 96/11953 and U.S. Pat. No. 4,179,337.

Ligation of the polypeptide binding agent with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

A polypeptide binding agent may be administered in its "naked" or unconjugated form, or may be conjugated directly to other therapeutic or diagnostic agents, or may be conjugated indirectly to carrier polymers comprising such other therapeutic or diagnostic agents. In some embodiments the polypeptide binding agent is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., (1986) supra). Suitable toxins include: bacterial toxins such as diphtheria toxin; plant toxins such as ricin; small molecule toxins such as geldanamycin (Mandler et al J. Natl. Cancer Inst. 92(19):1573-81 (2000); Mandler et al., Bioorg. Med. Chem. Letters 10:1025-1028 (2000); Mandler et al., Bioconjugate Chem. 13.786-91 (2002)), maytansinoids (EP 1391213; Liu et al., Proc. Natl. Acad. Sci. USA 93:8618-23 (1996)), auristatins (Doronina et al., Nat. Biotech. 21: 778-84 (2003) and calicheamicin (Lode et al., Cancer Res. 58:2928 (1998); Hinman et al., Cancer Res. 53:3336-3342 (1993)).

Polypeptide binding agents can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

Conjugation of polypeptide binding agent moieties is described in U.S. Pat. No. 6,306,393. General techniques are also described in Shih et al., Int. J. Cancer 41:832-839 (1988); Shih et al., Int. J. Cancer 46:1101-1106 (1990); and Shih et al., U.S. Pat. No. 5,057,313. This general method involves reacting a polypeptide binding agent component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated polypeptide binding agents can be prepared by directly conjugating a polypeptide binding agent component with a therapeutic agent. The general procedure is analogous to the indirect method of conjugation except that a therapeutic agent is directly attached to an oxidized polypeptide binding agent component. For example, a carbohydrate moiety of a polypeptide binding agent can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., Int. J. Cancer 56:244 (1994). General techniques for such conjugation are well-known in the art. See, for example, Wong, Chemistry Of Protein Conjugation and Cross-Linking (CRC Press 1991); Upeslacis et al., "Modification of Antibodies by Chemical Methods," in Monoclonal Antibodies: Principles and Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering and Clinical Application, Ritter et al. (eds.), pages 60-84 (Cambridge University Press 1995). A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., Ann. Oncol. 6:945 (1995), Nicolet et al., Cancer Gene Ther. 2:161 (1995), Becker et al., Proc. Nat'l Acad. Sci. USA 93:7826 (1996), Hank et al., Clin. Cancer Res. 2:1951 (1996), and Hu et al., Cancer Res. 56:4998 (1996). In addition, Yang et al., (*Hum. Antibodies Hybridomas* 6:129 (1995)), describe a fusion protein that includes an F(ab')$_2$ fragment and a tumor necrosis factor alpha moiety. Further examples of antibody fusion proteins are described by Pastan et al, Nat. Reviews Cancer 6: 559-65 (2006).

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., Nature 339:394 (1989), Brinkmann et al., Proc. Nat'l Acad. Sci. USA 88:8616 (1991), Batra et al., Proc. Nat'l Acad. Sci. USA 89:5867 (1992), Friedman et al., J. Immunol. 150:3054 (1993), Wels et al., Int. J. Can. 60:137 (1995), Fominaya et al., J. Biol. Chem. 271:10560 (1996), Kuan et al., Biochemistry 35:2872 (1996), and Schmidt et al., Int. J. Can. 65:538 (1996). Antibody-toxin fusion proteins containing a diphtheria toxin moiety have been described by Kreitman et al., Leukemia 7:553 (1993), Nicholls et al., J. Biol. Chem. 268:5302 (1993), Thompson et al., J. Biol. Chem. 270:28037 (1995), and Vallera et al., Blood 88:2342 (1996). Deonarain et al., Tumor Targeting 1:177 (1995), have described an antibody-toxin fusion protein having an RNase moiety, while Linardou et al., Cell Biophys. 24-25:243 (1994), produced an antibody-toxin fusion protein comprising a DNase I component. Gelonin was used as the toxin moiety in the antibody-toxin fusion protein of Wang et al., Abstracts of the 209th ACS National Meeting, Anaheim, Calif., Apr. 2-6, 1995, Part 1, BIOT005. As a further example, Dohlsten et al., Proc. Nat'l Acad. Sci. USA 91:8945 (1994), reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—A Cancer Journal for Clinicians 44:43 (1994). Other suitable toxins are known to those of skill in the art.

Antibodies herein may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful for purposes of the disclosure include, but are not limited to: alkaline phosphatase; arylsulfatase; cytosine deaminase, 5-fluorouracil; proteases, such as *serratia* protease, thermolysin, subtilisin, carboxypeptidases and cathepsins (such as cathepsins B and L); D-alanylcarboxypeptidases; carbohydrate-cleaving enzymes such as β-galactosidase and neuraminidase; β-lactamase; and penicillin amidases, such as penicillin V amidase or penicillin G amidase. Alternatively, antibodies with enzymatic activity, also known in the art as abzymes, can be used to convert prodrugs into free active drugs (See, e.g., Massey, Nature 328: 457-458 (1987). Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody described herein linked to at least a functionally active portion of an enzyme can be constructed using recombinant DNA techniques well known in the art (See, e.g., Neuberger et al., Nature 312: 604-608 (1984)).

Amino Acid Sequence Variants

It is contemplated that modified polypeptide compositions comprising one, two, three, four, five, and/or six CDRs of an antibody or polypeptide binding agent are generated, wherein a CDR or non-CDR region is altered to provide increased specificity or affinity to the antigen, or to provide increased modulation of binding affinity between the target and its signaling partner. For example, sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the targeted site. It is contemplated that conservative substitutions within the CDR allow the variable region to retain biological activity. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see e.g. Sambrook et al., Molecular Cloning: A Laboratory Manual, 2nd Edition, Cold Spring Harbor, N.Y. (1989)]. The amplified CDR sequences are ligated into an appropriate plasmid. The plasmid comprising one, two, three, four, five and/or six cloned CDRs optionally contains additional polypeptide encoding regions linked to the CDR.

Polypeptide binding agents comprising the modified CDRs are screened for binding affinity for the original antigen. Additionally, the antibody or polypeptide is further tested for its ability to neutralize the activity of its antigen. For example, antibodies herein may be analyzed as set out in the Examples to determine their ability to interfere with the biological activity of the target.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the invention are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., *Mol. Cell. Biol.* 8: 2159-2165 (1988)); the c-myc tag and the 8F9, 3C7, 6E10, G4, B7 and 9E10 antibodies thereto (Evan et al., *Mol. Cell. Biol.* 5:3610-16 (1985)); and the Herpes Simplex virus glycoprotein D (gD) tag and its antibody (Paborsky et al., *Protein Engineering* 3:547-53 (1990)). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Formulation of Pharmaceutical Compositions

To administer polypeptide binding agents to human or test mammals, it is preferable to formulate the polypeptide binding agent in a sterile composition comprising one or more sterile pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

The polypeptide binding agent is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site infusion pump or depot.

Pharmaceutical compositions useful in the present invention containing a polypeptide binding agent described herein as an active ingredient may contain sterile pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form used herein. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. A variety of aqueous carriers are suitable, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the polypeptide binding agent are prepared for storage by mixing the polypeptide binding agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, succinate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

In certain embodiments, an polypeptide binding agent used in the methods is in a pharmaceutical composition comprising one or more of a surfactant, an antioxidant, a stabilizer, an amino acid, and/or a sugar.

In various embodiments, the pharmaceutical composition comprising an antibody further comprises from 1-20 mM histidine, from 1-20 mM methionine, from 150 to 500 mM sorbitol, from 0.005 to 0.1% polysorbate 20, at pH 6.8 to 5.5.

The antibodies described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of polypeptide binding agent in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of polypeptide binding agent. A typical composition for intravenous infusion could be made up to contain 250 ml of sterile Ringer's solution, and 150 mg of polypeptide binding agent. Actual methods for preparing parenterally administrable compositions will be known or apparent to those skilled in the art and are described in more detail in, for example, Remington's Pharmaceutical Science, 15th ed., Mack Publishing Company, Easton, Pa. (1980). An effective dosage of polypeptide binding agent is within the range of 0.01 mg to 1000 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix (*J. Pharm. Sci.,* 85:1282-1285 (1996)) and Oliyai and Stella (*Ann. Rev. Pharmacol. Toxicol.,* 32:521-544 (1993)).

Administration and Dosing

In one aspect, the disclosure provides methods of administering a pharmaceutical composition comprising a negative modulator antibody as described herein.

Methods of the invention are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well. Suitable delivery devices may include those developed for the delivery of insulin (see e.g. Owens et al Diabetic Med. 20(11):886-898, 2003).

In one embodiment, administration is performed at the site of an affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations useful in the disclosure implanted at the site.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, or monthly.

Also contemplated in the present methods is the administration of multiple agents, such as an antibody composition in conjunction with a second agent as described herein.

The amounts of antibody composition in a given dosage will vary according to the size of the individual to whom the therapy is being administered as well as the characteristics of the disorder being treated. In exemplary treatments, it may be necessary to administer about 0.1 to about 25 mg/kg day, or from about 0.3 to 15 mg/kg, from about 0.3 to 9 mg/kg, or from about 1 to 6 mg/kg. Exemplary doses include, 0.1 mg/kg, 0.3 mg/kg, 0.5 mg/kg 1 mg/day, 0.75 mg/kg, 1.0 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg. Other doses include 1 mg/day, 2.5 mg/day, 5 mg/day, 10 mg/day, 20 mg/day, 25 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

Combination Therapy

It one embodiment, an antibody described herein is administered with a second agent useful to treat a disease or disorder as described herein. It is contemplated that two or more antibodies to different epitopes of the target antigen may be mixed such that the combination of antibodies together to provide still improved efficacy against a condition or disorder to be treated associated with the target polypeptide. Compositions comprising one or more antibody described herein may be administered to persons or mammals suffering from, or predisposed to suffer from, a condition or disorder to be treated associated with the target polypeptide.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A second agent may be other therapeutic agents, such as anti-diabetic agents, cytokines, growth factors, other anti-inflammatory agents, anti-coagulant agents, agents that will lower or reduce blood pressure, agents that will reduce cholesterol, triglycerides, LDL, VLDL, or lipoprotein(a) or increase HDL, agents that will increase or decrease levels of cholesterol-regulating proteins, anti-neoplastic drugs or molecules. For patients with a hyperproliferative disorder, such as cancer or a tumor, combination with second therapeutic modalities such as radiotherapy, chemotherapy, photodynamic therapy, or surgery is also contemplated.

Exemplary agents include, but are not limited to, acarbose, octreotide, verapamil, diazoxide and other agents useful to treat hypoglycemia or side effects associated with hypoglycemia.

It is contemplated the antibody and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the antibody composition. Prior administration refers to administration of the second agent within the range of one week prior to treatment with the antibody, up to 30 minutes before administration of the antibody. It is further contemplated that the second agent is administered subsequent to administration of the antibody composition. Subsequent administration is meant to describe administration from 30 minutes after antibody treatment up to one week after antibody administration.

It is further contemplated that other adjunct therapies may be administered, where appropriate. For example, the patient may also be administered a diet or food plan designed for a hypoglycemic patient, surgical therapy, or radiation therapy where appropriate.

It will also be apparent that dosing may be modified if traditional therapeutics are administered in combination with therapeutics described herein.

Methods of Use

It is contemplated herein that a negative modulator antibody that binds the INSR is useful to treat symptoms associated with hypoglycemia and hyperinsulinemia. In various embodiments, the disorder is post-prandial hypoglycemia associated with bariatric surgery.

Other conditions of hypoglycemia are recognized in the art and are discussed below. Certain of these symptoms are observed in post-prandial hypoglycemia and can inform how to treat and monitor treatment of post-prandial hypoglycemia with the antibodies described herein.

Congenital Hyperinsulinemia

Congenital hyperinsulinism is a condition that causes individuals to have abnormally high levels of insulin, resulting in frequent instances of low blood sugar (hypoglycemia). Repeated incidences of low blood sugar increase the risk for serious events such as breathing difficulties, seizures, intellectual disability, vision loss, brain damage, and coma. Mutations in several genes have been found to cause congenital hyperinsulinism and these mutations often result in over-secretion of insulin from beta cells and depletion of glucose from the blood stream.

There are currently only a few treatment approaches for persistent Congenital Hyperinsulinemia (CHI) [Arnoux J., et al. Orphanet Journal of Rare Diseases 6:63 (2011); Yorifuji T., Ann Pediatr Endocrinol Metab. 19:57-68 (2014)]. Diazoxide, a KATP channel activator, inhibits insulin secretion in pancreatic β-cells. The most frequent adverse effect is hypertrichosis (hirsutism). Other side effects include sodium and fluid retention which may precipitate congestive heart failure. Diazoxide is generally ineffective for those patients that have CHI due to KATP channel mutations, one of the most common causes of CHI. Octreotide is a somatostatin analog that inhibits insulin release. Although not approved for CHI, octreotide is utilized for diazoxide-unresponsive CHI. It is administered subcutaneously (SC) as multiple daily injections or continuously with a pump, or intravenously (IV) because of its short half-life (1 to 2 hours). Common adverse events include gastrointestinal symptoms and gall bladder complications. Partial pancreatectomy is an option for focal lesions and may be curative in a majority of the cases. However, lesions are not always visible or palpable at sites indicated by preoperative imaging. Patients with diffuse forms are primarily treated via continuous glucose feeds or off-label medications. Near-total pancreatectomy has been considered as a treatment, but this is characterized by a high risk of diabetes.

Insulinoma

Insulinoma is a tumor of the pancreas often starting in the beta cells, resulting in increased secretion of insulin. Treatment options for patients with insulinoma include medical therapy with diazoxide or somatostatin analogs to control hypoglycemic symptoms, but only surgical removal/partial pancreatectomy is curative. Insulinoma-induced hypoglycemia can recur years later after successful surgical removal (recurrence rate 5-7% in patients with sporadic insulinoma).

Approximately 5-10% of insulinomas (corresponding to ~125 new patients annually) are malignant and metastatic. 3 Malignant insulinomas generally respond poorly to traditional chemotherapeutic agent regimens; therefore, there is a high unmet need for glycemic control in this population. In addition, an insulin-targeting treatment that could be administered simultaneously with chemotherapy to control hypoglycemia would be of interest.

Post-Prandial Hypoglycemia

Post-prandial hyperinsulinemic hypoglycemia has recently been observed as a side effect or complication of gastric bypass surgery (Singh et al., Diabetes Spectrum 25: 217-221, 2012; Patti et al., Diabetologia 48:2236-2240, 2005; Service et al. N Engl J Med 353:249-254, 2005). Common methods for gastric bypass surgery include the Roux-en-Y gastric bypass method (RYGB), sleeve gastrectomy (Li et al., Surgical Laparoscopy, Endoscopy & Percutaneous Techniques 24:1-11, 2014), gastric banding or gastroplasty. An often observed side effect of gastric bypass surgery is "dumping" which is consequence of the ingestion of simple sugars and rapid emptying of food into the small intestine. This is often characterized by vasomotor symptoms (flushing, tachycardia), abdominal pain, and diarrhea. Late dumping, or a form of reactive hypoglycemia, can occur up to a few hours after eating and results from insulin response to hyperglycemia resulting from rapid absorption of simple sugars from the proximal small intestine. In contrast to dumping, which is noted soon after surgery and improves with time, hyperinsulinemic hypoglycemia presents several months to years (usually around 1 year, up to 3 yrs) after gastric bypass surgery. This syndrome is differentiated from dumping by onset of severe post-prandial neuroglycopenia, which is typically absent in dumping, as well as pancreatic nesidioblastosis (islet cell enlargement, β-cells budding from ductal epithelium, and islets in apposition to ducts). Unlike with dumping, nutrition modification does not alleviate the symptoms of post-prandial hypoglycemia (PPH).

Diagnosis and confirmation of hyperinsulinemic hypoglycemia after bariatric surgery is often based on observation of elevated insulin (>3 μU/ml) and C-peptide (>0.6 ng/ml) and a negative oral hypoglycemic agent screen (Service F. J., Endocrinol Metab Clin North Am 28:501-517, 1999).

In general, hypoglycemia may be mild and lead to symptoms such as anxiety and hunger, but patients are also at risk for severe hypoglycemia, which can cause seizures, coma, and even death. Typical symptoms associated with hypoglycemia that patients complain about include tiredness, weakness, tremulous and hunger. Many patients have to eat frequently to prevent symptoms from the low blood sugar. Some patients may develop psychiatric symptoms because of the low blood sugar.

It is contemplated that administration of an antibody that is a negative modulator of insulin signaling will be beneficial in the treatment of PPH after bariatric surgery. It is contemplated that the method is useful after any of the gastric surgeries known in the art and described herein, including but not limited to, Roux-en-Y gastric bypass method (RYGB), sleeve gastrectomy, gastric banding or gastroplasty. In one aspect, the hypoglycemia/hyperinsulinemia is treated using an, allosteric, monoclonal antibody to the human insulin receptor (INSR) that negatively modulates insulin actions. In one aspect, the antibody has one or more of the following characteristics selected form the group consisting of binding to both forms of the INSR (A and B), inhibiting INSR auto-phosphorylation, inhibiting INSR signaling via Akt, is specific, can inhibit binding of insulin, and does not bind to IGF-1R or affect IGF-1R signaling.

It is hypothesized that an antibody contemplated for use herein will confer cellular resistance to insulin through negative modulation of the INSR, thereby increasing and normalizing blood glucose levels in hyperinsulinemic patients. In various embodiments, the antibody reduces hyperinsulinemia or excess insulin signaling. In various embodiments, the administration increases post-prandial blood glucose in the subject by 1.5 to 10 fold, or 10 to 40%. In various embodiments, the administration increases postprandial blood glucose in the subject by approximately 10 mg/dL. In various embodiments, the administration increases blood glucose back into the normal range.

Additionally, the kinetics for hypoglycemia following meals can be ameliorated by an antibody described herein. For example, post-meal hypoglycemia of approximately <70 mg/dL or <60 mg/dL may occur 1-4 hrs post-meal. Treatment with an antibody as described herein is contemplated to reduce such post meal levels toward normal, non-symptomatic ranges. Such reduction can be by about 10-30 mg/dL, e.g., reduction may be about 10, 15, 20, 25, or 30 mg/dL or ore, or any amount in between these numbers.

Effects of administration of negative modulator antibodies to subjects are measured in vivo and in vitro. In one embodiment, it is contemplated that antibodies that negatively modulate insulin/insulin receptor activity decrease insulin sensitivity and in vivo levels of HbA1c, and glucose. These factors are measured using techniques common to those of skill in the art.

Subjects receiving a negative modulator antibody also may show improved: insulin secretion, glycemic control (as measured by glucose tolerance test (GTT) or mixed meal test (MMT)), insulin sensitivity as measured by insulin tolerance test (ITT)), beta-cell function (as measured by, e.g., cell mass, insulin secretion, C-peptide levels), beta-cell dormancy, and/or dyslipidemia.

For example, the ADA recommends a HbA1c target level of less than 7% in adults. For children, the ADA recommends higher target levels of A1c. In children younger than 6 years old, the recommended level is from 7.5% to 8.5%. In children 6 to 12 years old, the recommended level is less than 8%. the recommended level for teens 13 to 19 years old, is less than 7.5%. A1c is a measure of how well blood sugar levels have remained within a target range over the previous 2 to 3 months. (American Diabetes Association, Diabetes Care, 28(1): 186-212, 2005.) It is contemplated that administration of an antibody to treat PPH brings A1c levels towards that observed in a non-hypoglycemic individual, e.g., increasing A1c levels in a patient by an absolute HbA1c percentage measurement of at least 0.5%, 0.7%, 1.0% or 1.5% or more. Beta cells in the pancreatic islets of Langerhans make and release insulin, a hormone that controls the level of glucose in the blood. There is a baseline level of insulin maintained by the pancreas, but it can respond quickly to spikes in blood glucose by releasing stored insulin while simultaneously producing more. The response time is fairly rapid. For example, in Type 1 diabetes, progressive and extensive loss of beta cells results in decreased levels of secreted insulin, eventually leading to hyperglycemia (abnormally high level of glucose in the blood). In Type 2 diabetes, beta cells initially compensate for insulin resistance in a subject by increasing insulin output, but, over time, the cells become unable to produce enough insulin to maintain normal glucose levels. It is thought that both resistance of target tissues to the action of insulin and decreased insulin secretion, in part due to beta cell failure, occur.

Additional parameters that are measured for improvement include reduction in the frequency of hyperglycemic events (blood glucose>200 mg/dL), reduction in the frequency of hypoglycemic events (blood glucose<60 mg/dL), improvement of insulin levels, c-peptide levels, ketone levels, and free fatty acid levels.

It is contemplated that one or more of the parameters or outcome measures described herein is improved by at least about 10%, 20%, 30%, 40%, 50%, 60%, 70% or more, or by at least about 1, 1.5, 2., 2.5, 3, 4, 5, 6, 7, 8, 9, 10-fold or more.

EXAMPLES

Example 1

An Anti-INSR Negative Modulator Antibody Increases Fasting Blood Glucose

In order to determine the ability of the anti-INSR negative modulator antibody to affect hyperinsulinemic hypoglycemia, a negative modulator antibody was administered in a mouse knockout model of congenital hyperinsulinemia (SUR1−/− mice).

Wild-type or Sur1 knockout mice (n=10/group) were administered anti-KLH control mAb or Ab081 at a dose of 30 mg/kg via intraperitoneal injection on Days 1, 3, 7 and 10. Animals were monitored for fed and fasting blood glucose levels and serum insulin levels up to Day 22.

Administration of Ab081 increased fasting blood glucose levels from a hypoglycemic level to a normoglycemic level (or above) in Sur1 knockout mice up to Day 22 relative to the control group (FIG. 1). Also observed was an increase in fed blood glucose levels and in fasting serum insulin levels.

Additional studies were carried out in rats and monkeys. Ab081 reverses exogenous hyperinsulinemic hypoglycemia in rats at a dose of approximately 10 mg/kg.

Intravenous infusion of Ab081 to normal rats and monkeys yields increased fed and fasting insulin levels at 3-30 mg/kg, with rat appearing more sensitive than monkey. The pharmacokinetic half-life of Ab081 in rats and monkeys is approximately 5 days.

These results demonstrate that Ab081 is safe in vivo and has a dose dependent effect on insulin and glucose levels.

Example 2

Toxicokinetics after Repeat Dose Studies in Sprague-Dawley Rats and Cynomolgus Monkeys Toxicology of Ab081 was also measured to analyze the safety profile of the antibody over a long period of time. Ab081 was administered weekly as an IV injection for four weeks to Sprague-Dawley rats and six weeks to cynomolgus monkeys. Dose levels ranged up to 90 mg/kg. Serum concentrations of Ab081 were determined using a validated electrochemiluminescence immunoassay (ECL) method. Noncompartmental analysis was performed for each study.

The antibody showed biexponential decline similar to other monoclonal antibodies. Dose proportionality was observed at dose levels up to 90 mg/kg dose. Mean half-life was approximately 6 days and the accumulation index was approximately 1.4 to 2 fold. There is no observed gender differences in the TK after Ab081 administration.

These results show that Ab081 demonstrates excellent toxicokinetic properties with linear pharmacokinetics, low clearance and a long half-life across rat and monkey species after 4 to 6 weeks of weekly administration.

Example 3

Administration of Anti-INSR Negative Modulator Antibody in Humans

A phase 1, double-blind, placebo-controlled, single ascending dose study was performed to assess the safety, tolerability, pharmacokinetics and pharmacodynamics of intravenous doses of Ab081 in healthy adult male subjects.

Four subjects in the sentinel cohort received four active drug and two patients received placebo. Three subjects in subsequent cohorts received active drug and one received placebo. Doses of 0.1, 0.3, 1, 3, 6 and 9 mg/kg administered in sequential cohorts, with dose escalation based on safety and pharmacokinetic (PK) review. Serum insulin, glucose, β-hydroxy butyrate, C-peptide and glucagon levels were monitored as potential biomarkers. Mixed meal tests (MMTs) were scheduled pre-dose at day −1 and post-dose at days 1, 2, 3 and 6. Once changes in insulin and glucose consistent with induced insulin resistance were observed in a cohort, a 15 minute insulin tolerance test (ITT) was performed in subsequent cohort(s) pre-dose on day −1 and post-dose on days 1, 2, 3 and 5 to assess insulin sensitivity. Subjects remained in-patient from day −1 or day −2 (cohorts with ITT) until day 7 after drug administration. Dosing was stopped at cohort 4 (3 mg/kg) after observation of pharmacologic effects consistent with drug-induced insulin resistance; overall, 14 active and 5 placebo doses were administered to a total of 19 subjects. Ab081 appeared to be well-tolerated; there were no serious or severe adverse events. All drug-related adverse events were mild (43/46) or moderate (3/46), and none required either concomitant medication or invasive procedures for management.

The morning fasting plasma glucose (FPG) levels were monitored throughout the study week. Table 2 below shows the FPG values measured at the same time each morning, equivalent to the average of 1- and 1.5-hour post-infusion time points of Day 1. On Day 1, shortly after Ab081 infusion, FPG levels were increased in a roughly dose-related manner. Thereafter, and up to Day 5, FPG levels were largely unchanged from baseline (Day −1) or placebo in the 0.1 and 0.3 mg/kg dose groups but were lowered in the 1 and 3 mg/kg dose groups. Day 7 values were largely consistent with baseline values.

TABLE 2

Mean (+SEM) Fasting Glucose Levels (mg/dL)

| Group | Day −1 | Day 1 | Day 2 | Day 3 | Day 5 | Day 7 |
|---|---|---|---|---|---|---|
| Placebo | 92.1 | 92.7 | 93.6 | 91.1 | 89.5 | 90.0 |
| N = 5 | (1.6) | (1.7) | (0.8) | (1.1) | (1.5) | (0.9) |
| 0.1 mg/kg | 86.8 | 91.1 | 84.4 | 84.6 | 81.3 | 79.6* |
| N = 4 | (2.4) | (3.7) | (1.4) | (1.0) | (0.9) | (1.9) |
| 0.3 mg/kg | 90.6 | 96.6 | 88.0 | 89.8 | 91.4 | 89.7 |
| N = 3 | (8.0) | (2.6) | (1.7) | (3.4) | (6.5) | (2.6) |
| 1 mg/kg | 93.1 | 104.8 | 84.0 | 86.6 | 85.1 | 87.7 |
| N = 3 | (2.9) | (5.9) | (3.1) | (1.6) | (3.2) | (1.6) |

TABLE 2-continued

Mean (+SEM) Fasting Glucose Levels (mg/dL)

| Group | Day −1 | Day 1 | Day 2 | Day 3 | Day 5 | Day 7 |
|---|---|---|---|---|---|---|
| 3 mg/kg | 92.1 | 102.2* | 79.4# | 83.0 | 83.9 | 85.4 |
| N = 4 | (0.8) | (3.3) | (3.1) | (2.8) | (0.9) | (1.9) |

*p < 0.05 vs Day −1 and Placebo
p < 0.05 vs Placebo

The morning fasting insulin (FPI) levels were monitored throughout the study week. Morning ITTs were performed on Days 2, 3, and 5 for the high-dose group. On Day 1, shortly after Ab081 infusion, FPI levels were increased approximately 7-fold over baseline at each of 0.3, 1, and 3 mg/kg treatment groups. On Day 2, FPI levels were even higher for the 1 mg/kg group than on Day 1. FPI levels after Ab081 infusion were elevated through Day 6 at the 1 and 3 mg/kg dose levels and in a dose-incremental manner (FIG. 2A and Table 3).

TABLE 3

Mean (±SEM) Fasting Insulin Levels (uIU/mL)

| Group | Day −1 | Day 1 | Day 2 | Day 3 | Day 6 |
|---|---|---|---|---|---|
| Placebo | 7.1 | 7.5 | 8.3 | 8.6 | 5.9 |
| N = 5 | (1.2) | (1.2) | (1.2) | (0.4) | (4.1) |
| 0.1 mg/kg | 4.6 | 13.7 | 7.9 | 9.1@ | 7.6 |
| N = 4 | (1.0) | (2.8) | (1.0) | (0.9) | (1.8) |
| 0.3 mg/kg | 6.0 | 21.7 | 8.1 | 16.1 | 12.7 |
| N = 3 | (2.8) | (7.7) | (2.1) | (6.1) | (4.2) |
| 1 mg/kg | 8.4 | 36.0 | 15.5 | 26.2* | 13.7 |
| N = 3 | (3.1) | (25.7) | (5.6) | (0.3) | (3.1) |
| 3 mg/kg | 6.2 | 40.5* | (NA - ITT) | (NA - ITT) | 26.2* |
| N = 4 | (0.9)^ | (7.2) | | | (3.7) |

^Day −2 values
NA = Not available

Figure 2B:
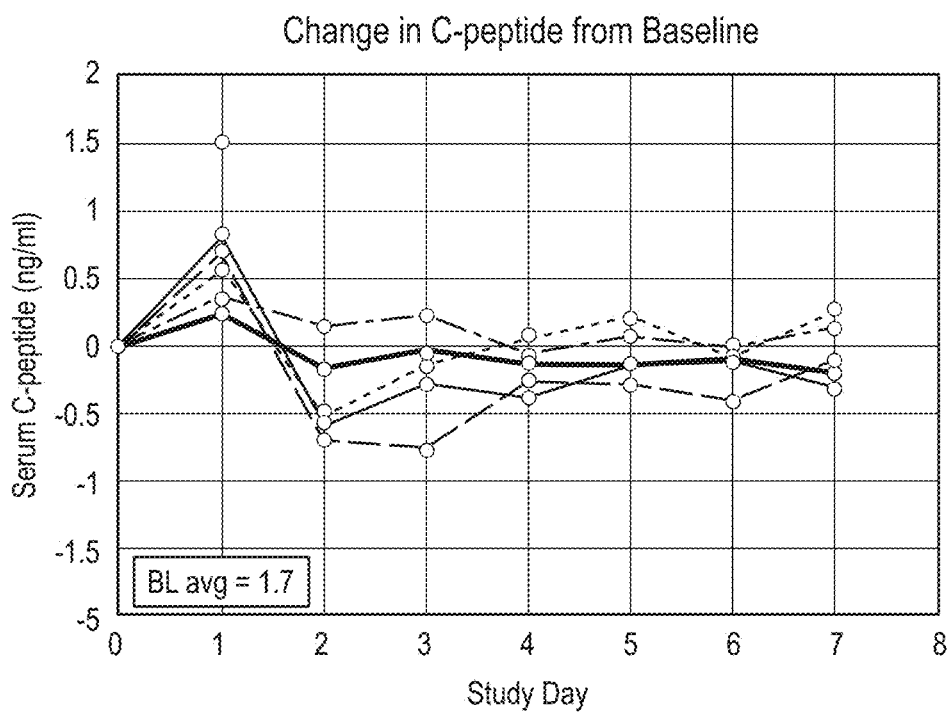

Results also show that the dose-dependent AM fasting serum insulin elevation occurred without significant C-peptide modulation (FIG. 2B).

Figure 3:
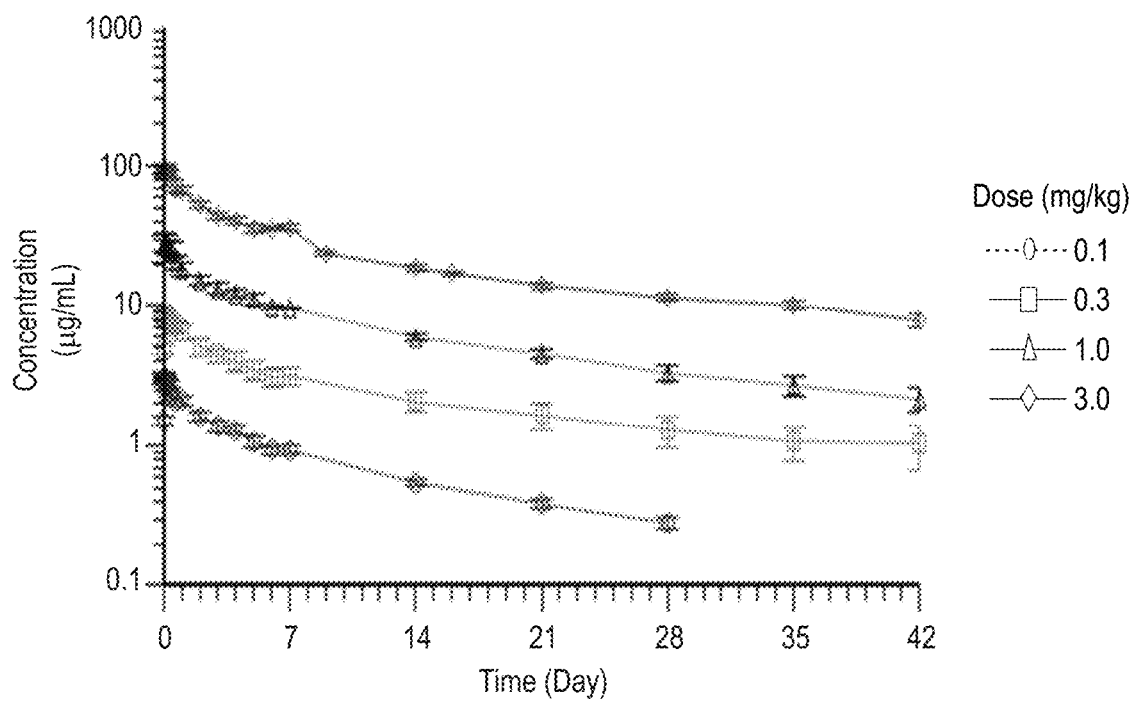
FIG. 3 shows that the pharmacokinetics (PK) in humans of Ab081 was linear with a drug half-life of approximately 14 days at the lowest dose and up to over 25 days at 3 mg/kg.

The PK of Ab081 was linear with a drug half-life of approximately 14 days at the lowest dose and up to over 25 days at 3 mg/kg. (FIG. 3 and Table 4).

TABLE 4

PK Parameters for Intravenous Ab081

| Dose (mg/kg) | $C_{max}$ (μg/ml) | $T_{max}$ (days) | $AUC_{0-inf}$ (μg/ml * day) | $t_{1/2}$ (days) | $V_{ss}$ (ml/kg) | CL (ml/day/kg) |
|---|---|---|---|---|---|---|
| 0.1 N = 3* | 3.3 ± 0.4 | 0.04 ± 0.03 | 29 ± 2.1 | 17 ± 1.5 | 73 ± 9.9 | 3.5 ± 0.3 |
| 0.3 N = 3 | 9.0 ± 0.6 | 0.04 ± 0.03 | 118 ± 38.3 | 22 ± 5.3 | 72 ± 6.6 | 2.9 ± 0.9 |
| 1 N = 3 | 29.4 ± 5.3 | 0.05 ± 0.02 | 324 ± 35.3 | 20 ± 4.7 | 77 ± 13.1 | 3.1 ± 0.4 |
| 3 N = 4 | 100.0 ± 7.1 | 0.06 ± 0.02 | 1150 ± 117 | 25 ± 3.9 | 79 ± 5.9 | 2.7 ± 0.3 |

Whole blood ketone levels under certain postprandial conditions (i.e., 2-hour post-dinner levels or MMT $AUEC_{0-2\ hr}$) did not appear to notably change in Ab081 treatment versus placebo groups or versus baseline values. Additionally, analysis of morning fasting levels at the +1-hour daily time point used in the glucose, insulin, and C-peptide fasting analyses did not reveal clear and consistent ketone changes after Ab081 treatment versus baseline or placebo AUCs.

Figure 4:
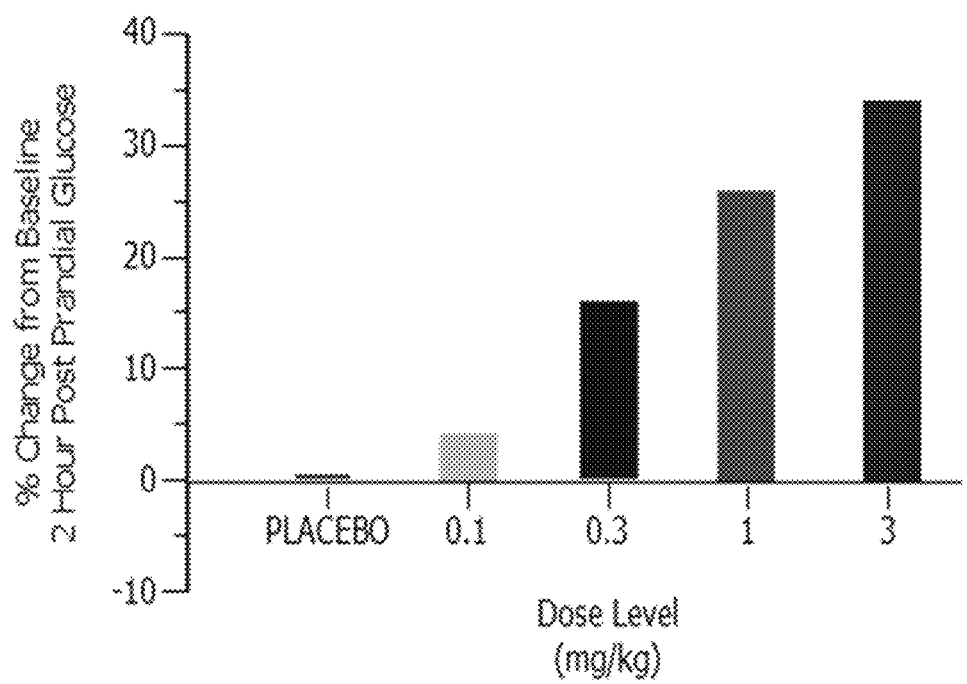
FIG. 4 shows dose-related increases in post-prandial glucose levels as measured in the MMTs were observed through day 6 following drug infusion.

Dose-related increases in post-prandial glucose levels as measured in the MMTs were observed through Day 6 following drug infusion, with the Day 3 glucose AUC nearly 80% greater than placebo at the 1 mg/kg dose level (FIG. 4).

Fasting HOMA-IR values, a measure of Ab081-induced insulin resistance, were likewise elevated by Ab081 in a dose-dependent manner and at peak time points, ranged from 2 to 9-fold over baseline for 0.1 to 3 mg/kg doses, respectively (Table 5). Relative to baseline or to placebo controls, Ab081 infusion resulted in dose-dependent increases in HOMA-IR that were most noticeable shortly post-infusion: Day 1 HOMA-IR values ranged from moderate (0.1 mg/kg) to severe (0.3, 1, 3 mg/kg) insulin resistance and seemed to peak with the 1 mg/kg dose level. The moderate to severe magnitudes of insulin resistance tended to persist throughout the week at the 0.3 through 3 mg/kg dose levels.

TABLE 5

Morning Fasting HOMA-IR[‡]

| Group | Day −1 | Day 1 | Day 2 | Day 3 | Day 4 | Day 5 | Day 6 | Day 7 |
|---|---|---|---|---|---|---|---|---|
| Placebo N = 5 | 1.7 (0.1) | 1.8 (0.4) | 2.0 (0.2) | 1.9 (0.1) | 1.2 (0.3) | 1.7 (1.2) | 1.3 (0.6) | 1.6 (0.6) |
| 0.1 mg/kg N = 4 | 1.0 (0.2) | 3.2[@] (0.6) | 1.7 (0.2) | 1.9 (0.2) | 1.4 (0.2) | 1.2 (0.1) | 1.5 (0.3) | 1.0 (0.1) |
| 0.3 mg/kg N = 3 | 1.4 (0.7) | *[5.8] [(1.9)]* | 1.8 (0.4) | 4.7 (1.6) | 3.4 (1.4) | 3.6 (1.6) | 2.7 (1.0) | 3.3 (1.5) |
| 1 mg/kg N = 3 | 2.0 (0.7) | *[10.2] [(6.9)]* | 3.3 (1.2) | *[5.7]\* [(0.0)]* | 3.4 (1.1) | 1.0 (0.7) | 2.9 (0.7) | 3.8 (1.1) |
| 3 mg/kg N = 4 | 1.4 (0.15)[#] | *[7.2]\* [(1.2)]* | NA | NA | **4.8\* (0.6)** | NA | *[5.3]\* [(0.9)]* | **3.8\* (0.7)** |

Figure 5:
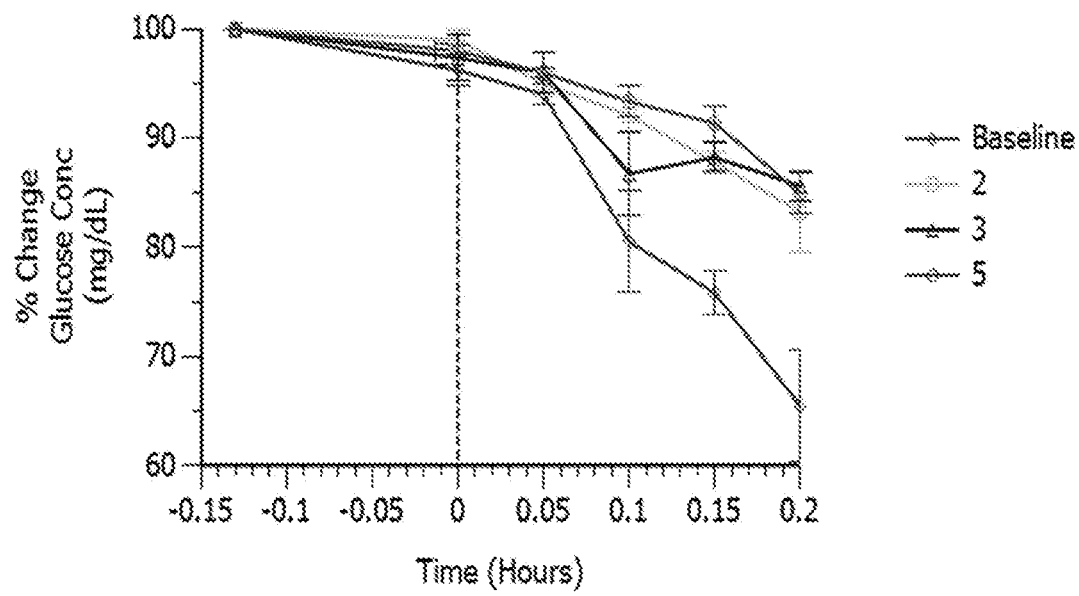
FIG. 5 shows a marked reduction in insulin sensitivity in an insulin tolerance test at the 3 mg/kg dose level.

[‡]Fasting HOMA-IR = fasting glucose (mg/dL) * fasting insulin (uIU/mL)/405
[#]Day −2 values
NA = Not applicable (ITT days)
bold: HOMA-IR value 3-5 = moderate insulin resistance
[bold italic]: HOMA-IR value ≥5 = severe insulin resistance A marked reduction in insulin sensitivity was verified via the ITT procedure at the 3 mg/kg dose level; markedly reduced $K_{ITT}$ values in the Ab081-treated subjects were observed relative to either placebo or baseline values (FIG. 5). The slope of insulin-induced glucose lowering was attenuated after Ab081 infusion versus baseline controls in each treated subject, and this shift appeared to be of a similar degree over Days 2-5.

An informative way of evaluating insulin changes during the ITT before and after Ab081 infusion was an AUEC determination from the time points of pre-insulin dosing through 0.23-hour post IV insulin administration. Table 6 below summarizes such data:

TABLE 6

| Days | 3 mg/kg XOMA Ab081 (N = 4) | Placebo (N = 1) |
|---|---|---|
| −1 (Baseline) | 80 ± 32* | 100 |
| 2 | 100 ± 20 | 85 |
| 3 | 137 ± 15 | 107 |
| 5 | 140 ± 17[#] | 104 |

[#]n = 3 (missing data for #4003)
Parameters are presented as Mean ± SD
Source: Table 14.2.4.4

Analysis for the insulin ITT $AUEC_{-0.1\ to\ 0.23\ hr}$ yielded values of 80 uIU/ml*hr for Ab081-treated subjects at baseline, and 85-107 uIU/ml*hr for placebo-treated subjects. Ab081-treated subjects showed an increase post-infusion versus baseline (and versus placebo on Days 3 and 5) that seemed to plateau at Days 3-5.

Analysis of serum C-peptide and whole blood ketones during the ITT (for example, by AUEC analyses per the above examples) indicated trends toward increased levels on Day 2 (ketone) or Day 3 (C-peptide) but not with the consistency of the glucose or insulin changes presented above.

FIG. 6 shows Serum Drug Concentration Versus HOMA-IR for Ab081-Treated Subjects Across Days 1-7. The data suggests that serum antibody concentrations>10 μg/ml correlate with measurable insulin resistance by HOMA-IR through the week post-infusion.

Results herein show that the pharmacokinetics of Ab081 in humans are better than anticipated with a long half-life, from 14 up to 25 days in humans compared to 5 days in rats or 10 days in monkeys. Levels of circulating insulin, a biomarker of Ab081 infusion, were elevated in a generally dose-related fashion, evident at the lowest tested dose (0.1 mg/kg), and were sustained at 0.3 mg/kg and higher dose levels for nearly 1 week. Increases in post-prandial glucose were evident at 0.3 mg/kg and higher and lasted through Day 5, at the higher dose levels. Drug-induced insulin resistance, as measured by morning fasting HOMA-IR, was evident at 0.3 mg/kg and higher. An ITT in the 3 mg/kg dose cohort confirmed Ab081-induced insulin resistance, evident within 2 days of IV infusion and sustained for at least 4 days post administration.

Dosing herein reveals that serum insulin can act as a biomarker to evaluate antibody administration and pharmacodynamic indicators of insulin resistance, such as MMT and ITT, establish that doses from 0.3-3.0 mg/kg are effective at modulating insulin and glucose levels. Additionally, the study shows favorable potency and no safety or tolerability issues were observed.

Example 4

Administration of Negative Modulator Anti-INSR Antibody to Post-Bariatric Surgery Patients In order to assess the effect of an antibody as described herein in patents that have undergone gastric bypass surgery, post-surgery patients will be administered a single dose and/or multiple doses of an anti-INSR negative modulator antibody and the effects on insulin and glucose levels measured.

Patients eligible for treatment will undergo a mixed meal test to determine if a certain meal type provokes hypoglycemia. The MMT is administered at day 0, day 7 and day 14, and optionally at day 4, and a determination of provocation of hypoglycemia is determined.

Doses of 0.1, 0.3, 1, 3, 6, 9 or 12 mg/kg are administered to patients in a single dose study as well as in a multiple dose study. Effects on serum insulin, glucose, β-hydroxy butyrate, C-peptide, glucagon, insulin and glucose levels are monitored using techniques described herein or known in the art.

It is expected that administration of the antibody will beneficially modulate blood and/or serum glucose levels, as well as improve hypoglycemic symptoms in these patients, or prevent onset of hypoglycemia if administered to patients without overt symptoms of post-prandial hypoglycemia. It is also hypothesized that administration of the antibody will lessen the magnitude and frequency of hypoglycemic events by modulating both glucose levels and other hypoglycemic symptoms.

Example 5

Single Dose Trial of Hypoglycemic Patients after Gastric Bypass Surgery

A single dose open label study is carried out to determine the efficacy of Ab081 in patients with hypoglycemia after gastric bypass surgery. Participants must have received gastric bypass surgery more than 1 year before dosing and postprandial hypoglycemia (blood glucose<60 mg/dL), or a drop in blood glucose near to this threshold and of a substantial magnitude as judged by the principal clinical investigator, must have occurred during the Baseline Period assessments.

Two groups are planned for evaluation, each group receiving a different dose of Ab081 as an IV infusion over 30 minutes. Group A receives a single 1 mg/kg IV dose of Ab081 as an infusion over 30 minutes on one occasion. The second dose level, for Group B, is determined after the Data Safety Review Committee (DSRC) has reviewed all available data relevant to the safety and tolerability, pharmacodynamics (PD), and pharmacokinetics (PK) of Ab081 collected through Day 12. The dose level of Group B is determined by the DSRC and will not exceed 3 mg/kg.

All standardized meals sum to the patient's daily caloric need and will contain approximately 10-35% protein, 20-35% fat, and 45% carbohydrate. Provocation meal testing is administered on Days 1, 2, 3, 5 and 11. On Days −3, −1, 1, 2, 3, 5 and 11, patients will consume a provocation meal consisting of BOOST® COMPACT (4 oz.) plus 1 teaspoon of sugar. Patients receive the provocation meal for breakfast. The provocation meal should be consumed within 15 minutes and served at the same time on each day. Fasting and postprandial blood samples are collected pre- and post-dose for insulin, c-peptide, glucose, ketones, glucagon, and free fatty acids.

Blood samples are collected for Ab081 on Day 1 before the start of infusion (pre-dose), at 30 minutes (immediately after the end of infusion), and at the following hours after the start of infusion: 1 hours, 2 hours, 3.5 hours, 11.5 hours, 24 (Day 2), 48 (Day 3), 72 (Day 4), 168 (Day 8), 240 (Day 11), 504 (Day 22) and 1008 (Day 43). Patients may be asked to follow-up, at the Investigator's discretion, for safety procedures, additional PK and PD sample collection, or both.

Analysis of the following parameters is carried out. Change in pharmacodynamic parameters from baseline, including glucose $AUC_{24}$, glucose $AUC_{0-6}$, fasting and postprandial glucose, insulin, c-peptide, ketones, free fatty acids; frequency of hypoglycemic events (blood glucose<60 mg/dL); frequency of hyperglycemic events (blood glucose>200 mg/dL); characterization of hypoglycemia as reflected in various measures, including the following: symptoms of hypoglycemia and blood glucose levels throughout the day, symptoms of hypoglycemia and blood glucose levels in response to a meal; and concomitant therapy/medications used during rescue.

The following non-compartmental PK parameters for Ab081 are calculated: $C_{max}$: maximum observed concentration, $T_{max}$: time of maximum observed concentration, $C_{EOI}$: observed concentration at the end of infusion, $k_{el}$: terminal elimination rate constant, $t_{1/2}$: terminal elimination half-life, $AUC_{0-t}$: area under the concentration-time curve from time zero to time of last quantifiable concentration, $AUC_{0-inf}$: area under the concentration-time curve from time zero to infinity, $C_L$: total drug clearance, $V_z$: apparent terminal phase volume of distribution, and $V_{SS}$: apparent volume of distribution at steady-state.

Blood glucose monitoring is performed through Day 22. Episodes of hypoglycemia are documented and treated as required. If a patient's blood glucose level is <60 mg/dL, rescue medication may be administered if deemed appropriate by the principal clinical investigator. Outpatients are instructed in the use of finger stick glucose meters and will continue to wear continuous glucose monitors. Patients will be trained on signs and symptoms of hypoglycemia, appropriate intervention, and documentation of any events in a patient diary. Glucose data will be collected via the continuous glucose monitoring system (CGMS) up to Day 22.

A 24-hour Holter cardiac monitor analysis may be performed, if feasible, during the Baseline period on Day −1 and during the treatment period post-dose on Day 3. Frequency of arrhythmic episodes during hypoglycemia and changes in QT interval (as measured by 24-hr Holter) are also assessed. Hepatic ultrasound is performed per the Investigator's standard practice, at Baseline, Day 12, and Day 29.

Physical examinations, including ECG and hepatic ultrasound analysis, and body height and weight measurement is also performed throughout the trial time period. Standardized meals are provided on all study days.

It is expected that administration of the antibody will improve hypoglycemic events and related symptoms in these patients, or prevent onset of hypoglycemia if administered to patients without overt symptoms of post-prandial hypoglycemia.

Numerous modifications and variations in the invention as set forth in the above illustrative examples are expected to occur to those skilled in the art. Consequently only such limitations as appear in the appended claims should be placed on the invention.

What is claimed:

1. A method of treating post-prandial hypoglycemia following bariatric surgery, comprising administering to a subject in need thereof an antibody that is a negative modulator of insulin binding to the insulin receptor and/or insulin action at the insulin receptor in an amount effective to ameliorate post-prandial hypoglycemia, wherein the antibody comprises three heavy chain CDRs set out in SEQ ID NO: 11-13 and three light chain CDRs set out in SEQ ID NO: 26-28.

2. The method of claim 1, wherein the antibody binds to (i) insulin receptor or (ii) a complex comprising insulin and insulin receptor, or both (i) and (ii), with an equilibrium dissociation constant KD of $10^{-5}$M or less that is capable of weakening the binding affinity between insulin and insulin receptor by at least about 3-fold.

3. The method of claim 1 wherein the antibody is capable of weakening the binding affinity between said insulin and insulin receptor by about 3-fold to 500-fold.

4. The method of claim 3, wherein the antibody increases the $EC_{50}$ of insulin signaling activity by about 2-fold to 1000-fold, as measured in a pAKT assay.

5. The method of claim 1, wherein the variable heavy chain is set out in SEQ ID NO: 1 and the variable light chain is set out in SEQ ID NO: 6.

6. The method of claim 1, wherein said antibody is a monoclonal antibody.

7. The method of claim 1, wherein said antibody is a human antibody.

8. The method of claim 1, wherein the antibody is conjugated to a hydrophobic moiety.

9. The method of claim 1, wherein the antibody is in a pharmaceutical composition.

10. The method of claim 1, wherein the antibody reduces hyperinsulinemia or excess insulin signaling.

11. The method of claim 1, wherein the subject has a blood glucose level of less than 70 mg/dL prior to administration.

12. The method of claim 1, wherein the antibody is administered at a dose of from 0.1 to 25 mg/kg.

13. The method of claim 1, wherein the antibody is administered at a dose of from 0.3. to 9.0 mg/kg.

14. The method of claim 1, wherein the antibody is administered once per week, once every two weeks, or once a month.

15. The method of claim 1, wherein the half-life of the antibody is approximately 14 to 25 days.

16. The method of claim 1, wherein the antibody is administered intravenously, intraarterially, intraperitoneally, intramuscularly, intradermally, subcutaneously, orally or by continuous infusion.

17. The method of claim 1, wherein administration increases post-prandial blood glucose in the subject by 1.5 to 10 fold or by 10 to 40%.

18. The method of claim 1, wherein administration increases post-prandial blood glucose in the subject by at least 10 mg/dL.

19. The method of claim 1, wherein the administration induces insulin resistance.

20. The method of claim 19, wherein insulin resistance is measured by meal tolerance test, insulin tolerance test or fasting HOMA-IR assay.

21. The method of claim 1, wherein the patient is also on a restricted diet regimen.

22. The method of claim 1, further comprising administering a second agent.

23. The method of claim 1, wherein the administration ameliorates one or more symptoms of post-prandial hypoglycemia selected from the group consisting of pancreatic nesidioblastosis, islet cell enlargement, islet cell hyperplasia, α cell budding, tachycardia, diaphoresis, and flushing.

24. The method of claim 1, wherein the administration takes place during a fasting regimen.

* * * * *

UNITED STATES PATENT AND TRADEMARK OFFICE
CERTIFICATE OF CORRECTION

PATENT NO. : 10,711,067 B2
APPLICATION NO. : 15/555608
DATED : July 14, 2020
INVENTOR(S) : Kirk W. Johnson et al.

Page 1 of 1

It is certified that error appears in the above-identified patent and that said Letters Patent is hereby corrected as shown below:

In the Claims

At Column 74, Line 66, "NO: 11-13" should be -- NOs: 11-13 --.

At Column 74, Line 67, "NO: 26-28." should be -- NOs: 26-28. --.

At Column 75, Line 4, "KD" should be -- $K_D$ --.

At Column 75, Line 7, "claim 1" should be -- claim 2, --.

At Column 75, Line 32, "0.3." should be -- 0.3 --.

At Column 76, Line 29, "α" should be -- β --.

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 40

<210> SEQ ID NO 1
<211> LENGTH: 118
<212> TYPE: PRT
<213> ORGANISM: Homo sapiens

<400> SEQUENCE: 1

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Met Asp Val Trp Gly Gln Gly Thr
            100                 105                 110

Thr Val Thr Val Ser Ser
        115
```

<210> SEQ ID NO 2
<211> LENGTH: 122
<212> TYPE: PRT
<213> ORGANISM: Homo sapiens

<400> SEQUENCE: 2

```
Gln Met Gln Leu Val Gln Ser Gly Ala Glu Val Lys Lys Thr Gly Glu
1               5                   10                  15

Ser Leu Lys Ile Ser Cys Gln Gly Tyr Gly Tyr Arg Phe Thr Asp Asn
            20                  25                  30

Trp Ile Gly Trp Val Arg Gln Met Pro Gly Arg Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Glu Trp Ser Ser Leu Lys Ala Ser Asp Thr Ala Met Tyr Tyr Cys
                85                  90                  95

Ala Arg His Ala Pro Leu Ala Val Ala Gly Met Ala Leu Gly Asp Trp
            100                 105                 110

Gly Gln Gly Thr Leu Val Thr Val Ser Ser
        115                 120
```

<210> SEQ ID NO 3
<211> LENGTH: 119
<212> TYPE: PRT
<213> ORGANISM: Homo sapiens

<400> SEQUENCE: 3

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ser Tyr
65                  70                  75                  80

Leu Gln Trp Ser Ser Leu Arg Ala Ser Asp Thr Ala Met Tyr Tyr Cys
                85                  90                  95

Ala Arg Leu Gly Ser Gly Trp Tyr Gly Asn Asp Tyr Trp Gly Gln Gly
                100                 105                 110

Thr Leu Val Thr Val Ser Ser
            115
```

```
<210> SEQ ID NO 4
<211> LENGTH: 119
<212> TYPE: PRT
<213> ORGANISM: Homo sapiens

<400> SEQUENCE: 4

Gln Val Gln Leu Gln Gln Ser Glu Ala Glu Leu Val Lys Pro Gly Ala
1               5                   10                  15

Ser Val Lys Ile Ser Cys Lys Ala Ser Gly Tyr Thr Phe Ser Ser Tyr
                20                  25                  30

Trp Met Asn Trp Val Lys Gln Arg Pro Gly Lys Gly Leu Glu Trp Ile
            35                  40                  45

Gly Gln Ile Tyr Pro Gly Asp Gly Asp Thr Asn Tyr Asn Val Lys Phe
        50                  55                  60

Lys Gly Lys Ala Thr Leu Thr Ala Asp Lys Ser Ser Gly Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Ser Gly Tyr Gly Ala Met Asp Tyr Trp Gly Gln Gly
                100                 105                 110

Thr Ser Val Thr Val Ser Ser
            115
```

```
<210> SEQ ID NO 5
<211> LENGTH: 119
<212> TYPE: PRT
<213> ORGANISM: Homo sapiens

<400> SEQUENCE: 5

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Arg Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Val Asp Lys Ser Ile Ser Thr Ala Tyr
65                  70                  75                  80
```

Leu Gln Trp Ser Ser Leu Lys Ala Ser Asp Thr Ala Met Tyr Tyr Cys
                85                  90                  95

Ala Thr His His Ala Ser Gly Arg Gly Leu Asp Pro Trp Gly Gln Gly
            100                 105                 110

Thr Leu Val Thr Val Ser Ser
        115

<210> SEQ ID NO 6
<211> LENGTH: 112
<212> TYPE: PRT
<213> ORGANISM: Homo sapiens

<400> SEQUENCE: 6

Asp Val Val Met Thr Gln Ser Pro Leu Ser Leu Ser Val Thr Leu Gly
1               5                   10                  15

Gln Pro Ala Ser Ile Ser Cys Arg Ser Ser Leu Ser Leu Val Tyr Gly
            20                  25                  30

Asp Glu Asn Thr Tyr Leu Asn Trp Phe Gln Gln Arg Pro Gly Gln Ser
        35                  40                  45

Pro Arg Arg Leu Leu Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

<210> SEQ ID NO 7
<211> LENGTH: 110
<212> TYPE: PRT
<213> ORGANISM: Homo sapiens

<400> SEQUENCE: 7

Gln Thr Val Val Thr Gln Glu Pro Ser Phe Ser Val Ser Pro Gly Gly
1               5                   10                  15

Thr Val Thr Leu Thr Cys Gly Leu Ser Ser Gly Ser Val Ser Thr Gly
            20                  25                  30

Tyr Ser Pro Gly Trp Tyr Gln Gln Thr Pro Gly Gln Ala Pro Arg Thr
        35                  40                  45

Leu Val Tyr Asn Thr Asn Thr Arg Ser Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Tyr Met Gly Ser
                85                  90                  95

Gly Thr Tyr Val Phe Gly Gly Gly Thr Lys Leu Thr Val Leu
            100                 105                 110

<210> SEQ ID NO 8
<211> LENGTH: 108
<212> TYPE: PRT
<213> ORGANISM: Homo sapiens

<400> SEQUENCE: 8

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Thr

```
                20                  25                  30
Ser Trp Tyr Gln Gln Lys Pro Gly Gln Ala Pro Val Leu Val Ile Phe
            35                  40                  45
Gly Lys Asn Asn Arg Pro Ser Gly Ile Pro Asp Arg Phe Ser Gly Ser
 50                  55                  60
Ser Ser Gly Asn Thr Ala Ser Leu Thr Ile Thr Gly Ala Gln Ala Glu
 65                  70                  75                  80
Asp Glu Ala Asp Tyr Tyr Cys Asn Ser Arg Asp Ser Ser Gly Asn Tyr
                85                  90                  95
Ala Val Phe Gly Gly Gly Thr Gln Leu Thr Val Leu
            100                 105
```

<210> SEQ ID NO 9
<211> LENGTH: 111
<212> TYPE: PRT
<213> ORGANISM: Homo sapiens

<400> SEQUENCE: 9

```
Asp Leu Val Leu Thr Gln Ser Pro Ala Ser Leu Ala Val Ser Leu Gly
 1               5                  10                  15
Gln Arg Ala Thr Ile Ser Cys Arg Ala Ser Lys Ser Val Ser Thr Ser
                20                  25                  30
Gly Tyr Ser Tyr Ile His Trp Tyr Gln Gln Lys Pro Gly Gln Pro Pro
            35                  40                  45
Lys Leu Leu Ile Tyr Leu Ala Ser Asn Leu Glu Ser Gly Val Pro Ala
 50                  55                  60
Arg Phe Ser Gly Ser Gly Ser Gly Thr Asp Phe Thr Leu Asn Ile His
 65                  70                  75                  80
Pro Val Glu Glu Glu Asp Ala Ala Thr Tyr Tyr Cys Gln His Asn Arg
                85                  90                  95
Glu Leu Arg Thr Phe Gly Gly Gly Thr Lys Leu Glu Ile Lys Arg
            100                 105                 110
```

<210> SEQ ID NO 10
<211> LENGTH: 115
<212> TYPE: PRT
<213> ORGANISM: Homo sapiens

<400> SEQUENCE: 10

```
Gln Ala Met Leu Thr Gln Pro Ala Ser Leu Ser Ala Ser Pro Gly Ala
 1               5                  10                  15
Ser Ala Ser Leu Thr Cys Thr Leu Arg Ser Gly Ile Asn Val Val Ala
                20                  25                  30
Tyr Asn Ile Tyr Trp Tyr Arg Gln Lys Ser Gly Ser Pro Pro Gln Ser
            35                  40                  45
Val Leu Arg Tyr Lys Ser Asp Ser Asp Ser Glu Arg Asp Ser Gly Val
 50                  55                  60
Pro Ser Arg Phe Ser Gly Ser Lys Asp Val Ser Ala Asn Ala Gly Ile
 65                  70                  75                  80
Leu Leu Ile Ser Gly Leu Gln Ser Glu Asp Glu Ala Asp Tyr Tyr Cys
                85                  90                  95
Leu Ile Trp His Asn Ser Ala Trp Val Phe Gly Gly Gly Thr Gln Leu
            100                 105                 110
Thr Val Leu
 115
```

```
<210> SEQ ID NO 11
<211> LENGTH: 8
<212> TYPE: PRT
<213> ORGANISM: Artificial Sequence
<220> FEATURE:
<223> OTHER INFORMATION: H-CDR1

<400> SEQUENCE: 11

Gly Phe Thr Phe Ser Ser Tyr Ala
1               5

<210> SEQ ID NO 12
<211> LENGTH: 8
<212> TYPE: PRT
<213> ORGANISM: Artificial Sequence
<220> FEATURE:
<223> OTHER INFORMATION: H-CDR2

<400> SEQUENCE: 12

Ile Ser Tyr Asp Gly Ser Asn Lys
1               5

<210> SEQ ID NO 13
<211> LENGTH: 11
<212> TYPE: PRT
<213> ORGANISM: Artificial Sequence
<220> FEATURE:
<223> OTHER INFORMATION: H-CDR3

<400> SEQUENCE: 13

Ala Arg His Glu Trp Gly Phe Gly Met Asp Val
1               5                   10

<210> SEQ ID NO 14
<211> LENGTH: 8
<212> TYPE: PRT
<213> ORGANISM: Artificial Sequence
<220> FEATURE:
<223> OTHER INFORMATION: H-CDR1

<400> SEQUENCE: 14

Gly Tyr Arg Phe Thr Asp Asn Trp
1               5

<210> SEQ ID NO 15
<211> LENGTH: 8
<212> TYPE: PRT
<213> ORGANISM: Artificial Sequence
<220> FEATURE:
<223> OTHER INFORMATION: H-CDR2

<400> SEQUENCE: 15

Ile Tyr Pro Gly Asp Ser Glu Thr
1               5

<210> SEQ ID NO 16
<211> LENGTH: 15
<212> TYPE: PRT
<213> ORGANISM: Artificial Sequence
<220> FEATURE:
<223> OTHER INFORMATION: H-CDR3

<400> SEQUENCE: 16

Ala Arg His Ala Pro Leu Ala Val Ala Gly Met Ala Leu Gly Asp
1               5                   10                  15

<210> SEQ ID NO 17
```

```
<211> LENGTH: 8
<212> TYPE: PRT
<213> ORGANISM: Artificial Sequence
<220> FEATURE:
<223> OTHER INFORMATION: H-CDR1

<400> SEQUENCE: 17

Gly Tyr Ser Phe Thr Ser Tyr Trp
1               5

<210> SEQ ID NO 18
<211> LENGTH: 8
<212> TYPE: PRT
<213> ORGANISM: Artificial Sequence
<220> FEATURE:
<223> OTHER INFORMATION: H-CDR2

<400> SEQUENCE: 18

Ile Tyr Pro Gly Asp Ser Asp Thr
1               5

<210> SEQ ID NO 19
<211> LENGTH: 12
<212> TYPE: PRT
<213> ORGANISM: Artificial Sequence
<220> FEATURE:
<223> OTHER INFORMATION: H-CDR3

<400> SEQUENCE: 19

Ala Arg Leu Gly Ser Gly Trp Tyr Gly Asn Asp Tyr
1               5                   10

<210> SEQ ID NO 20
<211> LENGTH: 8
<212> TYPE: PRT
<213> ORGANISM: Artificial Sequence
<220> FEATURE:
<223> OTHER INFORMATION: H-CDR1

<400> SEQUENCE: 20

Gly Tyr Thr Phe Ser Ser Tyr Trp
1               5

<210> SEQ ID NO 21
<211> LENGTH: 8
<212> TYPE: PRT
<213> ORGANISM: Artificial Sequence
<220> FEATURE:
<223> OTHER INFORMATION: H-CDR2

<400> SEQUENCE: 21

Ile Tyr Pro Gly Asp Gly Asp Thr
1               5

<210> SEQ ID NO 22
<211> LENGTH: 12
<212> TYPE: PRT
<213> ORGANISM: Artificial Sequence
<220> FEATURE:
<223> OTHER INFORMATION: H-CDR3

<400> SEQUENCE: 22

Ala Arg Gly Val Ser Gly Tyr Gly Ala Met Asp Tyr
1               5                   10

<210> SEQ ID NO 23
<211> LENGTH: 8
```

```
<212> TYPE: PRT
<213> ORGANISM: Artificial Sequence
<220> FEATURE:
<223> OTHER INFORMATION: H-CDR1

<400> SEQUENCE: 23

Gly Tyr Arg Phe Thr Ser Tyr Trp
1               5

<210> SEQ ID NO 24
<211> LENGTH: 8
<212> TYPE: PRT
<213> ORGANISM: Artificial Sequence
<220> FEATURE:
<223> OTHER INFORMATION: H-CDR2

<400> SEQUENCE: 24

Ile Tyr Pro Gly Asp Ser Asp Thr
1               5

<210> SEQ ID NO 25
<211> LENGTH: 12
<212> TYPE: PRT
<213> ORGANISM: Artificial Sequence
<220> FEATURE:
<223> OTHER INFORMATION: H-CDR3

<400> SEQUENCE: 25

Ala Thr His His Ala Ser Gly Arg Gly Leu Asp Pro
1               5                   10

<210> SEQ ID NO 26
<211> LENGTH: 11
<212> TYPE: PRT
<213> ORGANISM: Artificial Sequence
<220> FEATURE:
<223> OTHER INFORMATION: L-CDR1

<400> SEQUENCE: 26

Leu Ser Leu Val Tyr Gly Asp Glu Asn Thr Tyr
1               5                   10

<210> SEQ ID NO 27
<211> LENGTH: 3
<212> TYPE: PRT
<213> ORGANISM: Artificial Sequence
<220> FEATURE:
<223> OTHER INFORMATION: L-CDR2

<400> SEQUENCE: 27

Lys Val Ser
1

<210> SEQ ID NO 28
<211> LENGTH: 7
<212> TYPE: PRT
<213> ORGANISM: Artificial Sequence
<220> FEATURE:
<223> OTHER INFORMATION: L-CDR3

<400> SEQUENCE: 28

Met Gln Gly Thr His Trp Pro
1               5

<210> SEQ ID NO 29
<211> LENGTH: 9
<212> TYPE: PRT
```

```
<213> ORGANISM: Artificial Sequence
<220> FEATURE:
<223> OTHER INFORMATION: L-CDR1

<400> SEQUENCE: 29

Ser Gly Ser Val Ser Thr Gly Tyr Ser
1               5

<210> SEQ ID NO 30
<211> LENGTH: 3
<212> TYPE: PRT
<213> ORGANISM: Artificial Sequence
<220> FEATURE:
<223> OTHER INFORMATION: L-CDR2

<400> SEQUENCE: 30

Asn Thr Asn
1

<210> SEQ ID NO 31
<211> LENGTH: 9
<212> TYPE: PRT
<213> ORGANISM: Artificial Sequence
<220> FEATURE:
<223> OTHER INFORMATION: L-CDR3

<400> SEQUENCE: 31

Ala Leu Tyr Met Gly Ser Gly Thr Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: L-CDR1

<400> SEQUENCE: 32

Ser Leu Arg Ser Tyr Tyr
1               5

<210> SEQ ID NO 33
<211> LENGTH: 3
<212> TYPE: PRT
<213> ORGANISM: Artificial Sequence
<220> FEATURE:
<223> OTHER INFORMATION: L-CDR2

<400> SEQUENCE: 33

Gly Lys Asn
1

<210> SEQ ID NO 34
<211> LENGTH: 10
<212> TYPE: PRT
<213> ORGANISM: Artificial Sequence
<220> FEATURE:
<223> OTHER INFORMATION: L-CDR3

<400> SEQUENCE: 34

Asn Ser Arg Asp Ser Ser Gly Asn Tyr Ala
1               5                   10

<210> SEQ ID NO 35
<211> LENGTH: 10
<212> TYPE: PRT
<213> ORGANISM: Artificial Sequence
```

```
<220> FEATURE:
<223> OTHER INFORMATION: L-CDR1

<400> SEQUENCE: 35

Lys Ser Val Ser Thr Ser Gly Tyr Ser Tyr
1               5                   10

<210> SEQ ID NO 36
<211> LENGTH: 3
<212> TYPE: PRT
<213> ORGANISM: Artificial Sequence
<220> FEATURE:
<223> OTHER INFORMATION: L-CDR2

<400> SEQUENCE: 36

Leu Ala Ser
1

<210> SEQ ID NO 37
<211> LENGTH: 6
<212> TYPE: PRT
<213> ORGANISM: Artificial Sequence
<220> FEATURE:
<223> OTHER INFORMATION: L-CDR3

<400> SEQUENCE: 37

Gln His Asn Arg Glu Leu
1               5

<210> SEQ ID NO 38
<211> LENGTH: 9
<212> TYPE: PRT
<213> ORGANISM: Artificial Sequence
<220> FEATURE:
<223> OTHER INFORMATION: L-CDR1

<400> SEQUENCE: 38

Ser Gly Ile Asn Val Val Ala Tyr Asn
1               5

<210> SEQ ID NO 39
<211> LENGTH: 7
<212> TYPE: PRT
<213> ORGANISM: Artificial Sequence
<220> FEATURE:
<223> OTHER INFORMATION: L-CDR2

<400> SEQUENCE: 39

Tyr Lys Ser Asp Ser Asp Ser
1               5

<210> SEQ ID NO 40
<211> LENGTH: 8
<212> TYPE: PRT
<213> ORGANISM: Artificial Sequence
<220> FEATURE:
<223> OTHER INFORMATION: L-CDR3

<400> SEQUENCE: 40

Leu Ile Trp His Asn Ser Ala Trp
1               5
```